US007138550B2

(12) United States Patent
Carr et al.

(10) Patent No.: US 7,138,550 B2
(45) Date of Patent: Nov. 21, 2006

(54) BRIDGED CARBOCYCLIC COMPOUNDS AND METHODS OF MAKING AND USING SAME

(75) Inventors: Richard Van Court Carr, Allentown, PA (US); Thomas John Markley, Blandon, PA (US); Atteye Houssein Abdourazak, Allentown, PA (US); John Anthony Marsella, Allentown, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 205 days.

(21) Appl. No.: 10/784,377

(22) Filed: Feb. 23, 2004

(65) Prior Publication Data

US 2005/0037289 A1   Feb. 17, 2005

Related U.S. Application Data

(60) Provisional application No. 60/492,573, filed on Aug. 4, 2003.

(51) Int. Cl.
*C07C 43/18* (2006.01)
*C07C 43/188* (2006.01)
*G03C 1/492* (2006.01)

(52) U.S. Cl. ............... 568/667; 568/669; 568/670; 526/72; 549/417; 528/401; 528/402; 430/311

(58) Field of Classification Search ............. 568/667, 568/669, 670; 526/72; 549/417; 528/401, 528/402; 430/311
See application file for complete search history.

(56) References Cited

U.S. PATENT DOCUMENTS

| 6,291,130 | B1 | 9/2001 | Kodama et al. | 430/270.1 |
|---|---|---|---|---|
| 6,406,828 | B1 | 6/2002 | Szmanda et al. | 430/270.1 |
| 2002/0004570 | A1 | 1/2002 | Zampini et al. | 526/257 |
| 2002/0051936 | A1 | 5/2002 | Harada et al. | 430/270.1 |
| 2002/0055060 | A1 | 5/2002 | Taylor et al. | 430/270.1 |
| 2002/0061464 | A1 | 5/2002 | Aoai et al. | 430/270.1 |
| 2003/0059710 | A1 | 3/2003 | Inoue | 430/270.1 |

FOREIGN PATENT DOCUMENTS

| EP | 1103856 | 5/2001 |
|---|---|---|
| EP | 1126322 | 8/2001 |
| JP | 2179731 | 7/2002 |
| JP | 2004107277 A | 4/2004 |
| WO | WO 0017712 | 3/2000 |
| WO | WO 00/67072 | 11/2000 |
| WO | WO 0067072 | 11/2000 |
| WO | WO 0163362 | 8/2001 |
| WO | WO 0185811 | 11/2001 |
| WO | WO 0221212 | 3/2002 |
| WO | WO 0221213 | 3/2002 |
| WO | WO 0221214 | 3/2002 |
| WO | WO 0221216 | 3/2002 |
| WO | WO 0231595 | 4/2002 |

OTHER PUBLICATIONS

Hiroshi Ito, et al., "Synthesis and Evaluation of Alicyclic Backbone Polymers for 193 nm Lithography", American Chemical Society, 1998.
Hiroshi Ito, et al., "Aliphatic Platforms for the Design of 157 nm Chemically Amplified Resists", SPIE Proceedings, vol. 4690 (2002), 18-28.
M. M. Dhingra, et al., "Polymerization of 1,1,1Trifluoroacetone with Aliphatic Secondary Amines. A Proton and Fluorine Magnetic Resonance Invesitgation," Organic Magnetic Resonance, vol. 9, No. 1 (1977), pp. 23-28.
H. E. Simmons, et al., "Fluoroketones" The Central Research Department Station, E. I. du Pont de Nemours and Co., vol. 82 (1959), pp. 2288-2296.
E. T. McBee, et al., "The Chemistry of 1,1,1-Trifluoropropanone. II. The Reactions of 4-Methyl-1,1,1,-5,5,5-hexafluoro-3-penten-2-one with Methyimagnesium Iodide," The Department of Chemistry, Purdue University (1956), pp. 4597-4598.
A. L. Henne, et al., "Trifluoromethylated Butadienes," The Department of Chemistry at The Ohio State University (1954), pp. 5147-5148.
K. J. Pryzbilla, et al., "Hexafluoroacetone in Resist Chemistry: A Versatile New Concept for Materials for Deep UV Lithography," SPIE Advances in Resist Chemistry and Process IX vol. 1672 (1992).
M. K. Crawford, et al., "New Materials for 157 mn Photoresists: Characterization and Properties," SPIE Advances in Resist Chemistry and Processing IX vol. 3999 (2000).
R. R. Dammel, et al., "New Resin Systems for 157 nm Lithography," Journal of Photopolymer Science and Technology, vol. 14 No. 4 (2001).
H. Ito, et al., "Development of 157 nm Positive Resists," J. Vac. Sci. Technol. B 19(6) (2001).
H. Ito, "Dissolution Behavior of Chemically Amplified Resist Polymers for 248-, 193-, and 157-nm Lithography," J. Res. & Dev. vol. 45 No. 5 (2001).
S. Cho, et al., "Investigation of a Fluorinated ESCAP based resist for 157 nm Lithography," (2001).
K. Patterson, et al., "The Challenges in Materials Design for 157 nm Photoresists," Lithography, Solid State Technology, pp. 41-48 (2000).

*Primary Examiner*—Rosalynd Keys
(74) *Attorney, Agent, or Firm*—Michael K. Boyer

(57) ABSTRACT

Disclosed herein is a fluorinated bridged carbocyclic compound that can be polymerized by itself or with at least one other ethylenically unsaturated monomer to provide a polymer. The polymer may be used, for example, within a sub-300 nm photoresist composition. Also disclosed is a method to make the bridged carbocyclic compound.

37 Claims, 1 Drawing Sheet

BRIDGED CARBOCYCLIC COMPOUNDS AND METHODS OF MAKING AND USING SAME

CROSS REFERENCE TO RELATED APPLICATIONS

This application claims the benefit of U.S. Provisional Application No. 60/492,573, filed Aug. 4, 2003.

BACKGROUND OF THE INVENTION

The present invention relates generally to bridged carbocyclic compounds. This invention also relates to the use of these compounds, for example, as monomers that can be homopolymerized or copolymerized with other reactive components to make resins within sub-200 nanometer (nm) photoresist compositions.

Photoresists are photosensitive films that are used for the transfer of images to a substrate. In a typical lithography process, a substrate is generally coated with either a positive or negative photoresist coating. The photoresist-coated substrate is then exposed through a photomask to an activating radiation source which transfers the pattern of the photomask onto the photoresist-coated substrate. Depending upon whether the photoresist coating is positive or negative, the radiation source either increases or decreases its solubility in a subsequently applied developer solution. In a positive photoresist coating, the areas masked from the radiation source remain after development while the exposed areas are dissolved away whereas in a negative photoresist coating the opposite occurs. The patterned photoresist image acts as a mask for subsequent substrate patterning processes such as etching, doping, and/or coating with metals, other semiconductor materials, or insulating materials.

Current interest in the semiconductor industry has increased in photoresists that can be photoimaged with short wavelength radiation, i.e., exposure radiation of about 200 nm or less such as 193 nm (ArF laser) or 157 nm ($F_2$ excimer beam laser) wavelengths. Short exposure wavelengths may allow for the formation of smaller features within the semiconductor device. In this connection, a photoresist that can provide well-resolved images after exposure to a 193 nm or 157 nm wavelength radiation source may allow for the formation of relatively smaller (e.g., sub-0.25 μm) features. Smaller device features meet the industry demands for smaller dimension circuit patterns and provide for greater circuit density and enhanced device performance.

Photoresist materials, particularly sub-200 nm materials, are particularly challenging to develop because of the need to balance a variety of different performance characteristics. Photoresist materials should ideally provide high transparency at the exposure wavelength, sufficient resistance to plasma-etching processes, and functional groups that are capable of undergoing sufficient photochemical transformations that change the solubility in developer solutions. Besides these, other important characteristics include, but are not limited to, reasonably simple synthesis procedures, adhesion to the underlying substrate, glass transition temperatures compatible with typical processing temperatures, acceptable shelf storage lifetime, and minimum toxicological risk.

The prior art discloses a variety of monomers that can be polymerized and used as base resins within photoresist compositions for sub-200 nm applications. For the higher end of this range (e.g. 193 nm), cycloaliphatic structures have drawn the most attention. For lower wavelength applications (e.g. 157 nm), the monomers tend to have one or more electron-withdrawing groups such as fluorine or hydroxyl and one or more cyclic structures. It is believed that the combination of the electron-withdrawing groups and the one or more cyclic structures improve the performance of the photoresist composition, particularly transparency.

The preparation of bicyclo[2.2.1]hept-5-ene-2-(1,1,1-trifluoro-2-trifluoromethylpropan-2-ol), also known as NBHFA, and its use in photoresist polymers was first described by H. Ito, et al., "Synthesis and Evaluation of Alicyclic Backbone Polymers for 193 nm Lithography", American Chemical Society, 1998. Since then it has become an industry benchmark for 157 nm photoresists. The norbornene monomers disclosed therein were synthesized by a Diels-Alder Reaction. One reaction disclosed within the reference is as follows:

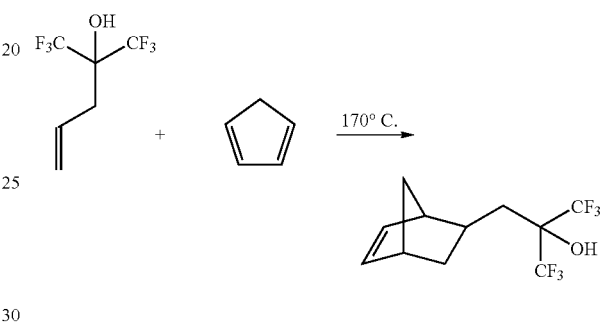

The optical density (OD) of the homopolymer (expressed as Absorption at 157 nm divided by the film thickness) was later reported to be 1.7 micrometers$^{-1}$ (Ito et al, SPIE Proceedings, Vol. 4690 (2002), 18–28).

U.S. Patent Application US2002/0004570 ("Zampini I") describes photoresist compositions that contain polymerized units of cyclic olefin monomers having one or more pendant cyclic electron-withdrawing groups. The pendant cyclic electron-withdrawing groups disclosed may be N-based, O-based, or S-based.

European published patent application WO 02/21214 ("Zampini II") discloses base resins within 157 nm photoresist compositions that contain at least one electronegative group that includes aromatic groups such as phenolic moieties. In this connection, Zampini II specifically describes vinyl ether entities that incorporate fluorinated aromatic structures as the electronegative group.

European published patent application WO 02/21213 ("Taylor") describes resins that are used within photoresist compositions that contain photoacid-labile deblocking groups substituted with one or more electron-withdrawing groups. The electron-withdrawing moieties within the resin are bonded to the blocking group so that the acid-catalyzed blocking and deblocking reactions are relatively unaffected by their presence.

Japanese Application JP 2002/179,731 (Chemical Abstracts 137:54625; "Harada I") discloses photoresist resins that contain the structure: $CO_2CR^1R^2R$ where $R^1$ and $R^2$=H, F, or a $C_{1-20}$ alkyl and R=$C_{3-20}$ cyclic alkyl. In addition, Harada I describes an acrylate resin that contains fluorinated alkyl groups in ester side chains.

U.S. Patent Application 2002/0051936 ("Harada II") describes an acrylic resin that contains repeating units containing a fluorinated hydrocarbon group, an acid labile group, and an adhesive group. Harada II describes one of the units, preferably the acid labile group, as having at least one alicyclic structure. Harada II also describes acrylic polymers containing the structure —O—C(R¹R²)—C(H)(R³)R⁴, where $R^1$, $R^2$, $R^3$, and $R^4$ are H, F, or an unsubstituted or fluorinated, straight, branched or cyclic alkyl group. Transparencies are reported from 25–45% for 200 nm films measured by transmission spectroscopy.

European Application EP 1 126 322 describes resins for use in a 157 nm photoresist that contain fluorinated ester groups. Transparencies are reported from 40–60% for 300 nm films measured by transmission spectroscopy.

European Application EP 1,103,856 ("Tsutsumi") describes a fluorine-containing resin that contains polymerized units of an acrylic or methacrylic acid ester wherein the ester moiety comprises a fluorine-containing group. Tsutsumi further describes moieties where the fluorine-containing group has a cyclic structure such as a fluorine-containing benzene ring, a fluorine-containing cyclopentane ring, a fluorine-containing cyclohexane ring, or a fluorine-containing cycloheptane ring. Transparencies are reported from 51–68% for 100 nm films measured by transmission spectroscopy.

US 0059710A1 discloses the following composition useful as a photoresist composition:

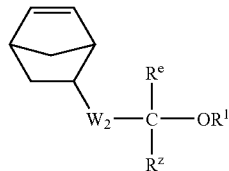

wherein $R^e$ is a hydrogen atom or an organic group; $W^2$ is a linkage group; $R^f$ is a hydrogen atom or a hydroxyl-protecting group; and $R^z$ is a group containing a fluorine atom, where carbon atoms constituting the ring in the formula may each have a substituent. Additionally, US 0059710A1 discloses in Example 14, the reaction of 5-hydroxybicyclo[2.2.1]-2-heptene and hexafluoroacetone to produce 5-[1,1-bis(trifluoromethyl)-1-hydroxymethyl]oxybicyclo[2.2.1]-2-heptene:

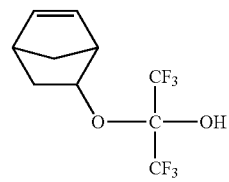

WO 00/67072 discloses the following composition useful as a photoresist

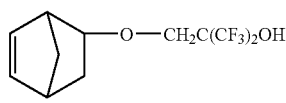

As described in Example 3 of WO 00/67072, the photoresist material was made by reacting sodium hydride, hexafluoroisobutylene epoxide, and 5-norbornene-2-methanol in anhydrous DMF. Sodium hydride is pyrophoric, making this process difficult to commercialize.

Many of the monomers that are known to be useful in a photoresist material must be copolymerized with fluoroolefins or the like to form a useful photoresist material, for example, see the "Binder 2 Preparation Procedure" on page 24 of WO 02/31595 A2 which uses 70 parts TFE in a pressurized vessel when making a copolymer to be used as a photoresist material. The tetrafluoroethylene provides improved transparency to the copolymer; however, the tetrafluoroethylene decreases the etch resistance, and causes poor adhesion, and additionally complicates the reaction to make the photoresist material.

Accordingly, there is a need in the art to provide novel resins polymerized from novel monomers that provide high transparency at sub-200nm wavelengths. These monomers can be used to make homopolymers useful as photoresist materials, if desired. There is also a need in the art for new industrial processes to make fluorine-containing monomers providing improved transparencies.

All references cited herein are incorporated herein by reference in their entirety.

BRIEF SUMMARY OF THE INVENTION

This invention provides a bridged carbocyclic compound comprising a bridged carbocyclic ring, and an alkoxide group, wherein an oxygen of the alkoxide group is bonded to a ring-member of said bridged carbocyclic ring and to a carbon of the alkoxide group, and further wherein the carbon of the alkoxide group bonded to said oxygen has at least one fluorine-containing group bonded to said carbon and further wherein the alkoxide group has at least one hydroxyl group separated from said carbon that is bonded to said oxygen and said fluorine-containing group by at least one additional carbon that is bonded to said carbon that is bonded to said oxygen.

This invention further provides a bridged carbocyclic compound having the following structure:

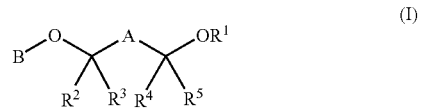

(I)

where A is a single bond, or a divalent organic group having 1 to 20 carbon atoms, and B is a bridged carbocyclic group of the type:

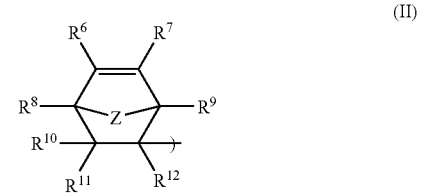

(II)

wherein Z is $CH_2$, $CHR^{13}$, $CR^{13}R^{14}$, $CH_2CH_2$, $CH_2CHR^{15}$, or a heteroatom; $R^1$ is a hydrogen, fluorinated alkylene alcohol group, or a fluorinated cycloalkylene alcohol group having 1 to 20 carbons; and $R^{2-15}$ are each independently a hydrogen atom, a fluorine atom, an alkyl group, a fluorinated alkyl group, a cycloalkyl group, a fluorinated cycloalkyl group, a hydroxyl group, an alkoxyl group, a fluorinated alkoxyl group, an acyl group, an acyloxy group, a fluorinated acyl group, a fluorinated acyloxy group, or any of the above groups having an amine group, or an ether group therein, with the proviso that at least one of $R^2$ and $R^3$ and at least one of $R^4$ and $R^5$ are independently a fluorine, a fluorinated alkyl group or a fluorinated cycloalkyl group. $R^3$ and $R^4$ may be any of the groups defined for $R^{2-15}$ and be bonded to each other to thereby form a 5 or 6 member ring including A, $R^3$, and $R^4$. The ring may contain heteroatoms. In an alternative embodiment, both of $R^3$ and $R^4$ are fluorine, fluorinated alkyl groups or fluorinated cycloalkyl groups. In an alternative embodiment, $R^{2-15}$ are each independently a hydrogen atom, a fluorine atom, a hydroxyl group, or comprises 1 to 20 carbons and is a fluorinated alkyl group, a fluorinated cycloalkyl group, an acyl group, an acyloxy group, a fluorinated acyl group, a fluorinated acyloxy group, an alkyl group, an alkoxyl group, a fluorinated alkoxyl group, or a cycloalkyl group (as described above.

In a further aspect of the present invention, there is provided a method for making a bridged carbocyclic compound by reacting a bridged carbocyclic reaction material and a fluorinated diol, and the methods of making and using photoresist compositions comprising bridged carbocyclic compounds are disclosed.

In yet another aspect of the present invention, there is provided a polymer comprising polymerized units of one or more bridged carbocyclic compounds of the invention. The novel polymers are transparent at wavelengths of 300 nm or less, or 200 nm or less. The novel polymers are transparent at 157 nm. The polymer has incorporated in it acidic protons to assist base solubility during the photoresist removal step prior to etching. The acidic protons can be blocked by acid labile groups. The polymers are used in photoresist compositions.

This invention further provides a bridged carbocyclic compound having the following structure:

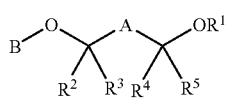

(I)

where A is a single bond, or a divalent organic group having 1 to 20 carbon atoms, and B is a bridged carbocyclic group of the type:

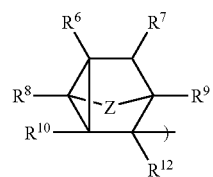

(III)

wherein Z is $CH_2$, $CHR^{13}$, $CR^{13}R^{14}$, $CH_2CH_2$, $CH_2CHR^{15}$, or a heteroatom; $R^1$ is a hydrogen, fluorinated alkylene alcohol group, or a fluorinated cycloalkylene alcohol group having 1 to 20 carbons; and $R^{2-10,12-15}$ are each independently a hydrogen atom, a fluorine atom, an alkyl group, a fluorinated alkyl group, a cycloalkyl group, a fluorinated cycloalkyl group, a hydroxyl group, an alkoxyl group, a fluorinated alkoxyl group, an acyl group, an acyloxy group, a fluorinated acyl group, a fluorinated acyloxy group, or any of the above groups having an amine group, an ether group therein, with the proviso that at least one of $R^2$ and $R^3$ and at least one of $R^4$ and $R^5$ is fluorine, a fluorinated alkyl group or a fluorinated cycloalkyl group. $R^3$ and $R^4$ may be any of the groups defined for $R^{2-15}$ and be bonded to each other to thereby form a 5 or 6 member ring including A, $R^3$, and $R^4$. The ring may contain heteroatoms. Preferably both of $R^3$ and $R^4$ are fluorine, fluorinated alkyl groups or fluorinated cycloalkyl groups. This composition of this invention comprising Structures I and III will be referred to as a nortricyclane compound. The preferred embodiments for the nortricyclane compound are the same as for the bridged carbocyclane compounds comprising Structure I and II described in detail below, except it comprises a nortricyclane ring as shown in Structure III, instead of the carbocyclane ring shown in Structure II. The nortricyclane compound can be used as a dissolution inhibitor by the incorporation of a protecting group. A dissolution inhibitor is added to the photoresist composition.

These and other aspects of the invention will become apparent from the following detailed description.

DETAILED DESCRIPTION OF THE INVENTION

Figure 1:
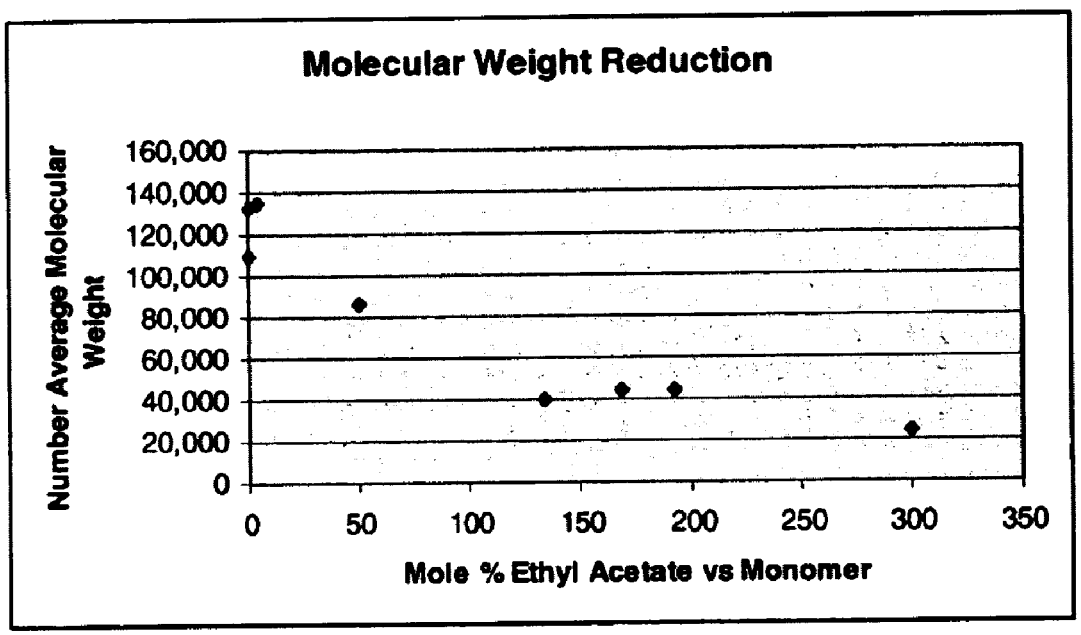
FIG. 1 is a plot of the affect of ethyl acetate on molecular weight for Example 22.

The present invention is directed to fluorine-containing bridged carbocyclic compounds and methods for making and using the same in, for example, a photoresist composition. The compound of the present invention may be polymerized by itself to provide a homopolymer or with other reactive monomers to provide a copolymer. The polymer of the present invention may be used, for example, in a sub-200 nm photoresist composition. The terms "resin" and "polymer" are used interchangeably throughout this specification to describe the polymer or copolymer of this invention useful in a photoresist composition.

The preferred method of making the compounds of this invention is by reacting bridged carbocyclic reaction material and fluorinated alcohols, preferably in a solvent, under conditions sufficient to effect a reaction to form the monomers. The bridged carbocyclic reaction materials include tetracyclo[3.2.0.0$^{2,7}$.0$^{4,6}$]heptane, which is commonly referred to as quadricyclane, tetracyclo[4.2.0.0$^{2,8}$.0$^{5,7}$]octane, a thioquadricyclane, an oxaquadricyclane, or a substituted derivative of quadricyclane, tetracyclo[4.2.0.0$^{2,8}$.0$^{5,7}$]octane, thioquadricyclane, or oxaquadricyclane. It was new, surprising and unexpected to produce fluorine-containing bridged carbocyclic compounds for use as monomers (and dissolution inhibitors) for photoresist resins using those reaction materials. The resulting highly fluorinated monomers are well-suited for 157 nm or other applications.

The present invention is directed, in part, to bridged carbocyclic compounds and methods of making and using same. They may be unsaturated (one double bond in the ring) alkoxy-substituted bridged carbocyclic compounds such as ethers of bicyclo-, oxabicyclo-, and thiabicycloalkenes. The compounds of the invention comprise a bridged carbocyclic ring, and an alkoxide group, wherein the oxygen of the alkoxide group is bonded to a ring member of said bridged carbocyclic ring and further wherein the carbon of said alkoxide group bonded to said oxygen further has at least one fluorine-containing group bonded to said carbon and wherein the alkoxide group has at least one hydroxyl group separated from said carbon, that is bonded to said oxygen and said fluorine-containing group, by at least one additional carbon that is bonded to said carbon that is bonded to said oxygen and to said fluorine-containing group. The alkoxide group may contain a ring. The alkoxide group may contain heteroatoms therein, such as oxygen, sulfur, a nitrogen group (e.g., N—H, N-alkyl, and N-acyl), and the like. The fluorine-containing groups include fluoroalkyl groups, fluorocyclic alkyl groups or a fluorine atom. The hydroxyl groups are hydroxyl groups preferably having a pKa<12. The carbon bonded to the —OH of the hydroxyl group may have one or two fluorine containing groups bonded thereto. As shown in Structure I, the alkoxide group includes O, $R^2$, $R^3$, A, $R^4$, $R^5$ and $OR^1$.

The preferred bridged carbocyclic compounds of this invention include:

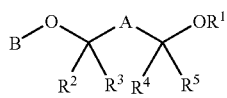

(I)

where A is a single bond, or a straight chain, branched or cyclic divalent organic group having 1 to 20 carbon atoms, and can include heteroatoms such as oxygen, sulfur, a nitrogen group (e.g., N—H, N-alkyl, and N-acyl), and the like, as well as substituents such as fluorine, fluoroalkyl groups, and hydroxyl groups.

Preferably A is a single bond, alkylene group, a hydroxyl substituted alkylene group, a fluorinated alkylene group, a hydroxyl substituted fluorinated alkylene group, a cycloalkylene group, a hydroxyl substituted cycloalkylene group, a fluorinated cycloalkylene group, or a hydroxyl substituted fluorinated cycloalkylene group with those groups having 1 to 15 carbon atoms, more preferably A is a single bond, alkylene group, a hydroxyl substituted alkylene group, a fluorinated alkylene group, a hydroxyl substituted fluorinated alkylene group, a cycloalkylene group, a hydroxyl substituted cycloalkylene group, a fluorinated cycloalkylene group, or a hydroxyl substituted fluorinated cycloalkylene group in those groups having 1 to 15 carbons. Specific examples of A include methylene; ethane-1,1-diyl (ethylidene); ethane-1,2-diyl (ethylene); propane-1,1-diyl; propane-1,2-diyl; propane-1,3-diyl; butane-1,1-diyl; butane-1,2-diyl; butane-1,3-diyl; butane-1,4-diyl; butane-2,3-diyl; pentane-1,1-diyl; pentane-1,2-diyl; pentane-1,3-diyl; pentane-1,4-diyl; pentane-1,5-diyl; hexane-1,6-diyl; 2-methylpropane-1,2-diyl; 2-methylpropane-1,3-diyl; 3-methylbutane-1,3-diyl; 2-methylbutane-1,3-diyl; 2-methylbutane-1,4-diyl; 2,3-dimethylbutane,-2,3-diyl; 2,5-dimethylhexane-1,6-diyl; 3-oxapentane-1,5-diyl; cyclopropane-1,1-diyl; cyclopropane-1,2-diyl; cyclobutane-1,1-diyl; cyclobutane-1,2-diyl; cyclobutane-1,3-diyl; cyclopentane-1,1-diyl; cyclopentane-1,2-diyl; cylopentane-1,3-diyl; cyclohexane-1,1-diyl; cyclohexane-1,2-diyl; cyclohexane-1,3-diyl; cyclohexane-1,4-diyl; methylcyclohexane-1,4-diyl; 1,1,2,2-tetrafluoroethane-1,2-diyl; 3,3,3-trifluoropropane-1,2-diyl; and 2-hydroxypropane-1,3-diyl;

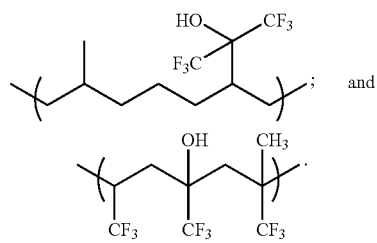

B is a bridged carbocyclic group of the type:

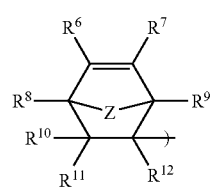

(II)

wherein Z is $CH_2$, $CHR^{13}$, $CR^{13}R^{14}$, $CH_2CH_2$, $CH_2CHR^{15}$, or a heteroatom, for example, oxygen, a nitrogen group (e.g., N—H, N-alkyl, and N-acyl) or sulfur, preferably Z is oxygen or $CH_2$, more preferably Z is $CH_2$.

$R^1$ is a hydrogen, a fluorinated alkylene alcohol group having 1–20 carbons, or a fluorinated cycloalkylene alcohol group having 1–20 carbons, preferably $R^1$ is hydrogen.

$R^{2-15}$ are each independently a hydrogen atom, a fluorine atom, an alkyl group, a fluorinated alkyl group, a cycloalkyl group, a hydroxyl group, a fluorinated cycloalkyl group, a hydroxyl group, an alkoxyl group, a fluorinated alkoxyl group, an acyl group, a fluorinated acyl group, an acyloxy group, a fluorinated acyloxy group, or any of the above groups having an amine group, or an ether group therein, wherein the alkyl group, fluorinated alkyl group, cycloalkyl group, fluorinated cycloalkyl group, acyl group, fluorinated acyl group, acyloxy group, fluorinated acyloxy group, alkoxyl group, or fluorinated alkoxyl group comprises from 1 to 20 carbons; with the proviso that at least one of $R^2$ and $R^3$ and at least one of $R^4$ and $R^5$ is a fluorine, a fluorinated alkyl group or a fluorinated cycloalkyl group. $R^3$ and $R^4$ may also be joined within their structures to form a ring, as illustrated by

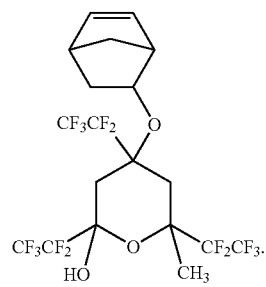

Preferably both $R^3$ and $R^4$ are fluorine, fluorinated alkyl groups or fluorinated cycloalkyl groups.

Preferably, $R^{2-15}$ are each independently a hydrogen atom, a fluorine atom, an alkyl group, a fluorinated alkyl group, a cycloalkyl group, a fluorinated cycloalkyl group, a hydroxyl group, an alkoxyl group, a fluorinated alkoxyl group, wherein the alkyl group, the fluorinated alkyl group, cycloalkyl group, fluorinated cycloalkyl group, alkoxyl, or fluorinated alkoxyl group comprises from 1 to 20 carbons, more preferably 1 to 10 carbons.

Preferably $R^{13-15}$ are each independently a fluorinated cyclo alkyl group having 1–10 carbons, a fluorinated alkyl group having 1–10 carbons, or a fluorine atom.

Preferably $R^{6-7}$ are each independently a fluorinated alkyl having 1–10 carbons, a fluorinated alkoxy group having 1–10 carbons, a hydrogen atom or a fluorine atom, more preferably both $R^6$ and $R^7$ are hydrogen atoms.

Preferably $R^{8-12}$ are each independently a fluorinated alkyl having 1–10 carbons, fluorinated alkoxy having 1–10 carbons, a hydrogen atom or a fluorine atom, more preferably all of $R^{8-12}$ are hydrogen atoms.

In some embodiments $R^1$ is a hydrogen, $R^4$ and $R^5$ are each independently a fluorinated alkyl groups having 1 to 5 carbons, a fluorinated cyclic alkyl group having 1 to 5 carbons or a fluorine atom. In an alternative embodiment $R^1$ is a hydrogen, and $R^2$, $R^3$, $R^4$ and $R^5$ are —$CF_3$. In the preferred embodiments, B is norbornenyl, or 7-oxanorbornenyl, preferably norbornenyl. The preferred fluorinated monomers of this invention have seven or more fluorine atoms, more preferable from nine to thirty-five fluorines, most preferably between from twelve to thirty fluorine atoms present on the fluorinated alcohol monomer molecule.

In some embodiments of the present invention, there is provided a norbornene compound of the formula (IV):

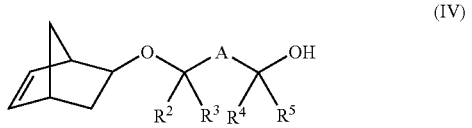

(IV)

where A and $R^{2-5}$ are as defined above. More preferably, A is a single bond or any linear or branched alkyl group having 1 to 6 carbons, or fluorinated alkyl group having 1 to 15 carbons, or cycloalkyl group having 4 to 6 carbons, or fluorinated cycloalkyl group having 4 to 6 carbons, and where $R^2$ is a hydrogen atom, a fluorine atom, an alkyl group having 1 to 6 carbons, a fluorinated alkyl group having 1 to 6 carbons, a cycloalkyl group having 4 to 6 carbons, or a fluorinated cyclo alkyl group having 4 to 6 carbons, and $R^{3-5}$ are independently fluorinated alkyl groups having 1 to 3 carbons or fluorinated cycloalkyl groups having 1 to 3 carbons. Most preferred, A is a single bond or any linear or branched alkyl group having 1 to 6 carbons or fluorinated alkyl group having 1 to 15 carbons or cycloalkyl group having 4 to 6 carbons or fluorinated cycloalkyl group having 4 to 6 carbons, and where $R^{2-5}$ are independently fluorinated alkyl groups having 1 to 3 carbons or a fluorinated cycloalkyl group having 1 to 3 carbons.

The term "alkyl" as used herein includes straight chain or branched groups, preferably containing from 1 to 20 carbon atoms, or more preferably from 1 to 10 carbon atoms. Exemplary alkyl groups include methyl, ethyl, n-propyl, isopropyl, n-butyl, isobutyl, sec-butyl, tert-butyl, tert-amyl, n-pentyl, and n-hexyl. The term "fluorinated" applies to moieties wherein one or more of its hydrogens are replaced by a fluorine atom, and may be partially or fully fluorinated. In certain embodiments, some of the alkyl groups may be substituted with one or more heteroatoms, such a halogen atom, or other heteroatoms such as O, N, or S. The term "cycloalkyl" refers to a cyclic alkyl structure, preferably containing from 3 to 20 carbon atoms e.g. cyclopentyl, or cyclohexyl, and fluorinated cycloalkyl applies to cycloalkyl moieties in which one or more of its hydrogens are replaced by a fluorine atom, and may be partially or fully fluorinated. In certain embodiments, some of the cycloalkyl groups may be substituted with a halogen or with one or more heteroatoms, such as O, N, or S. The term "alkoxyl" refers to a group having the following structure R'-O, where R' is an alkyl or cycloalkyl group as defined above including fluorinated derivatives thereof.

Bridged carbocyclic compounds (monomers) of the invention are as follows:

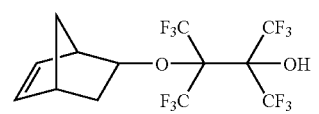

3-bicyclo[2.2.1]hept-5-en-2-yloxy-2,3-bis(trifluoromethyl)-1,1,1,4,4,4-hexafluorobutan-2-ol

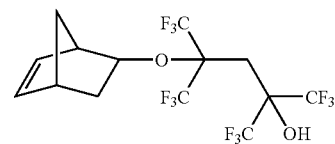

4-bicyclo[2.2.1]hept-5-en-2-yloxy-2,4-bis(trifluoromethyl)-1,1,1,5,5,5-hexafluoropentan-2-ol

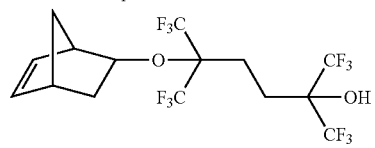

5-bicyclo[2.2.1]hept-5-en-2-yloxy-2,5-bis(trifluoromethyl)-1,1,1,6,6,6-hexafluorohexan-2-ol

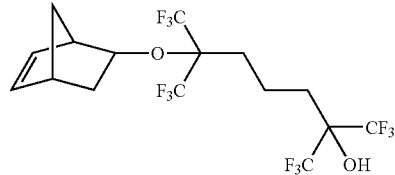

6-bicyclo[2.2.1]hept-5-en-2-yloxy-2,6-bis(trifluoromethyl)-1,1,1,7,7,7-hexafluoroheptan-2-ol

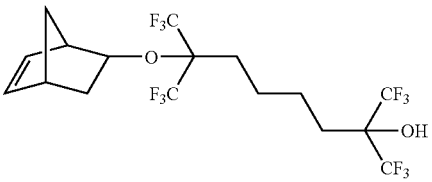

7-bicyclo[2.2.1]hept-5-en-2-yloxy-2,7-bis(trifluoromethyl)-1,1,1,8,8,8-hexafluorooctan-2-ol

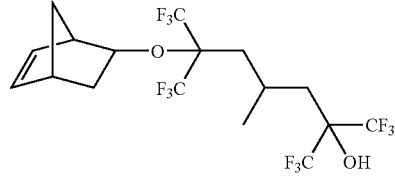

6-bicyclo[2.2.1]hept-5-en-2-yloxy-2,6-bis(trifluoromethyl)-1,1,1,7,7,7-hexafluoro-4-methylheptan-2-ol

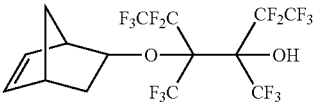

4-bicyclo[2.2.1]hept-5-en-2-yloxy-3,4-
bis(trifluoromethyl)-1,1,1,2,2,5,5,6,6,6-
decafluorohexan-3-ol

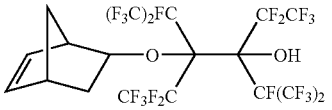

5-bicyclo[2.2.1]hept-5-en-2-yloxy-3,5-
bis(trifluoromethyl)-1,1,1,2,2,6,6,7,7,7-
decafluoroheptan-3-ol

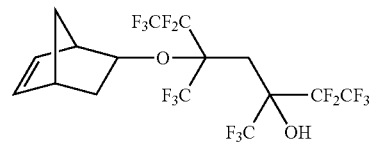

6-bicyclo[2.2.1]hept-5-en-2-yloxy-3,6-
bis(trifluoromethyl)-1,1,2,2,7,7,8,8,8-
nonafluorooctan-3-ol

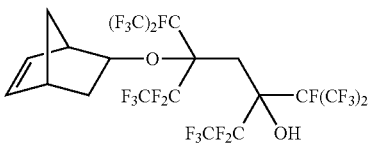

7-bicyclo[2.2.1]hept-5-en-2-yloxy-3,7-
bis(trifluoromethyl)-1,1,1,2,2,8,8,9,9,9-
decafluorononan-3-ol

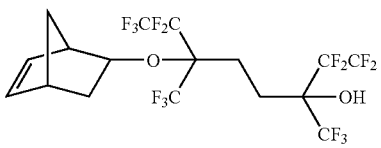

8-bicyclo[2.2.1]hept-5-en-2-yloxy-3,8-
bis(trifluoromethyl)-1,1,1,2,2,9,9,10,10,10-
decafluorodecan-3-ol

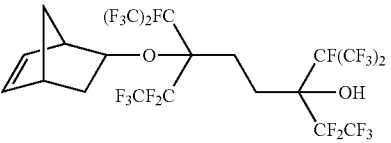

7-bicyclo[2.2.1]hept-5-en-2-yloxy-3,7-
bis(trifluoromethyl)-1,1,1,2,2,8,8,9,9,9-
decafluoro-5-methylnonan-3-ol

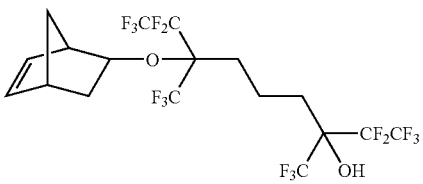

4-bicyclo[2.2.1]hept-5-en-2-yloxy-3,4-
bis[1,2,2,2-tetrafluoro-1-
(trifluoromethyl)ethyl]-1,1,1,2,2,5,5,6,6,6-
decafluorohexan-3-ol

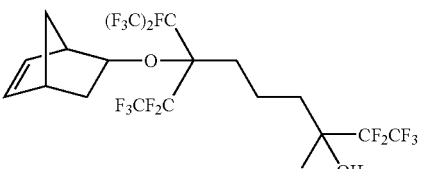

5-bicyclo[2.2.1]hept-5-en-2-yloxy-3,5-
bis[1,2,2,2-tetrafluoro-1-
(trifluoromethyl)ethyl]-1,1,1,2,2,6,6,7,7,7-
decafluoroheptan-3-ol

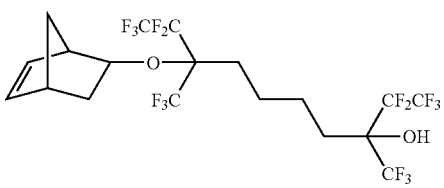

6-bicyclo[2.2.1]hept-5-en-2-yloxy-3,6-
bis[1,2,2,2-tetrafluoro-1-
(trifluoromethyl)ethyl]-1,1,1,2,2,7,7,8,8,8-
decafluorooctan-3-ol

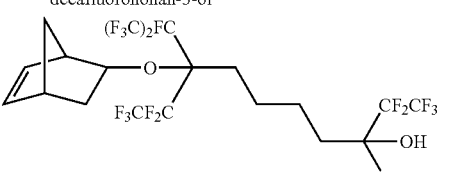

7-bicyclo[2.2.1]hept-5-en-2-yloxy-3,7-
bis[1,2,2,2-tetrafluoro-1-
(trifluoromethyl)ethyl]-1,1,1,2,2,8,8,9,9,9-
decafluorononan-3-ol

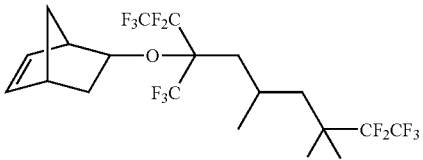

8-bicyclo[2.2.1]hept-5-en-2-yloxy-3,8-
bis[1,2,2,2-tetrafluoro-1-
(trifluoromethyl)ethyl]-
1,1,1,2,2,9,9,10,10,10-decafluorodecan-3-ol

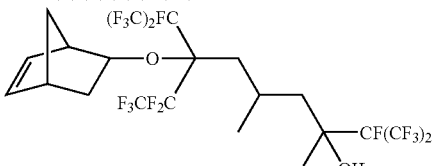

7-bicyclo[2.2.1]hept-5-en-2-yloxy-3,7-
bis[1,2,2,2-tetrafluoro-1-
(trifluoromethyl)ethyl]-1,1,1,2,2,8,8,9,9,9-
decafluoro-5-methylnonan-3-ol

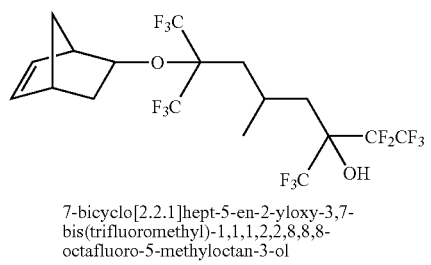

7-bicyclo[2.2.1]hept-5-en-2-yloxy-3,7-bis(trifluoromethyl)-1,1,1,2,2,8,8,8-octafluoro-5-methyloctan-3-ol

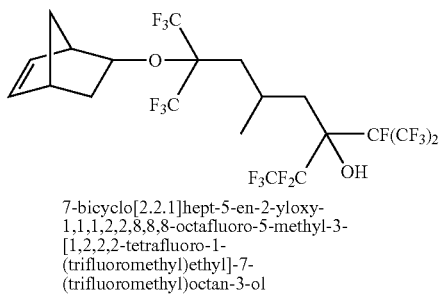

7-bicyclo[2.2.1]hept-5-en-2-yloxy-1,1,1,2,2,8,8,8-octafluoro-5-methyl-3-[1,2,2,2-tetrafluoro-1-(trifluoromethyl)ethyl]-7-(trifluoromethyl)octan-3-ol

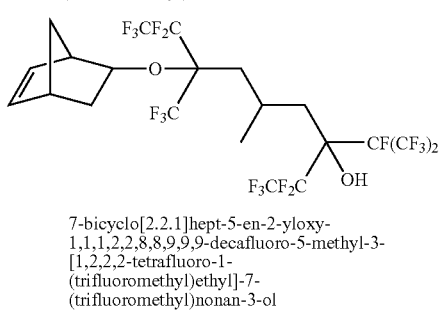

7-bicyclo[2.2.1]hept-5-en-2-yloxy-1,1,1,2,2,8,8,9,9,9-decafluoro-5-methyl-3-[1,2,2,2-tetrafluoro-1-(trifluoromethyl)ethyl]-7-(trifluoromethyl)nonan-3-ol

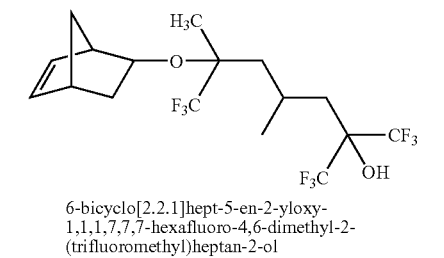

6-bicyclo[2.2.1]hept-5-en-2-yloxy-1,1,1,7,7,7-hexafluoro-4,6-dimethyl-2-(trifluoromethyl)heptan-2-ol

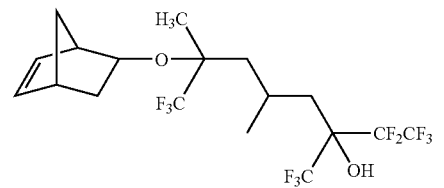

7-bicyclo[2.2.1]hept-5-en-2-yloxy-1,1,1,2,2,8,8,8-octafluoro-5,7-dimethyl-3-(trifluoromethyl)octan-3-ol

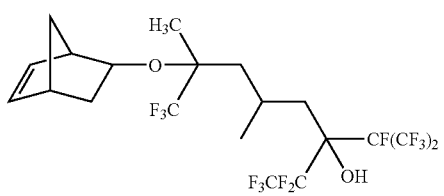

7-bicyclo[2.2.1]hept-5-en-2-yloxy-1,1,1,2,2,8,8,8-octafluoro-5,7-dimethyl-3-[1,2,2,2-tetrafluoro-1-(trifluoromethyl)ethyl]octan-3-ol

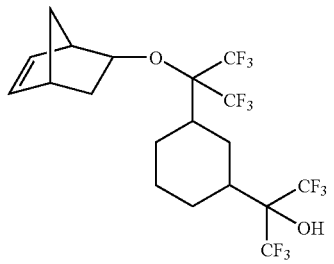

2-{3-[1-bicyclo[2.2.1]hept-5-en-2-yloxy-2,2,2-trifluoro-1-(trifluoromethyl)ethyl]cyclohexyl}-1,1,1,3,3,3-hexafluoropropan-2-ol

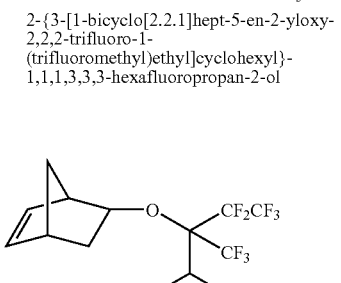

2-{3-[1-bicyclo[2.2.1]hept-5-en-2-yloxy-2,2,3,3,3-pentafluoro-1-(trifluoromethyl)propyl]cyclohexyl}-1,1,1,3,3,4,4,4-octafluorobutan-2-ol

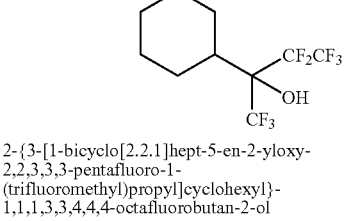

3-{3-[1-bicyclo[2.2.1]hept-5-en-2-yloxy-2,2,3,3,3-pentafluoro-1-[1,2,2,2-tetrafluoro-1-(trifluoromethyl)ethyl]propyl}cyclohexyl)-1,1,1,2,4,4,5,5,5-nonafluoro-2-(trifluoromethyl)pentan-3-ol

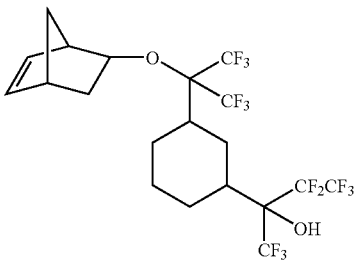

2-{3-[1-bicyclo[2.2.1]hept-5-en-2-yloxy-2,2,2-trifluoro-1-(trifluoromethyl)ethyl]cyclohexyl}-1,1,1,3,3,4,4,4-octafluorobutan-2-ol

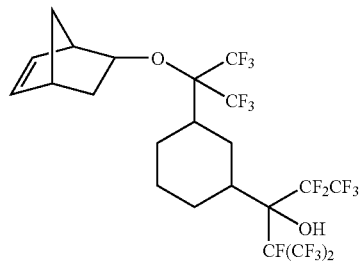

3-{3-[1-Bicyclo[2.2.1]hept-5-en-2-yloxy-
2,2,2-trifluoro-1-trifluoromethyl-ethyl]-
cyclohexyl}-1,1,1,2,2,4,5,5,5-nonafluoro-
4-trifluoromethyl-pentan-3-ol

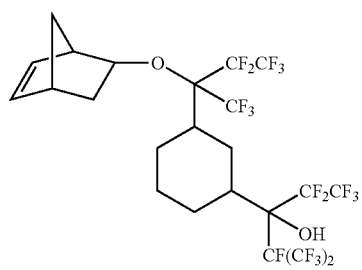

3-{3-[1-Bicyclo[2.2.1]hept-5-en-2-yloxy-
2,2,3,3,3-pentafluoro-1-trifluoromethyl-
propyl]-cyclohexyl}-1,1,1,2,2,4,5,5,5-
nonafluoro-4-trifluoromethyl-pentan-3-ol

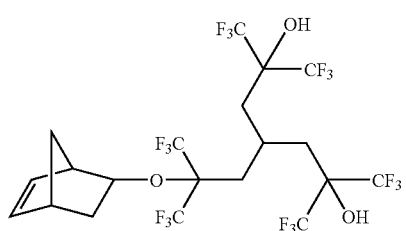

4-[bicyclo[2.2.1]hept-5-en-2-yloxy-
3,3,3-trifluoro-2-(trifluoromethyl)-
propyl]-2,6-bis(trifluoromethyl)-
1,1,1,7,7,7-hexafluoroheptane-2,6-diol

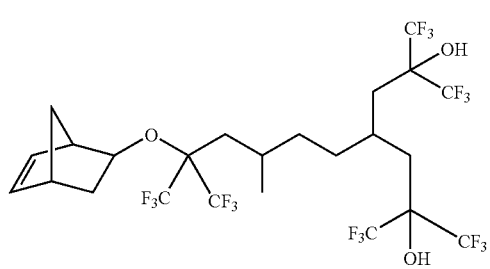

4-[bicyclo[2.2.1]hept-5-en-2-yloxy-
6,6,6-trifluoro-3-methyl-5-
(trifluoromethyl)hexyl]-2,6-
bis(trifluoromethyl)-1,1,1,7,7,7-
hexafluoroheptane-2,6-diol

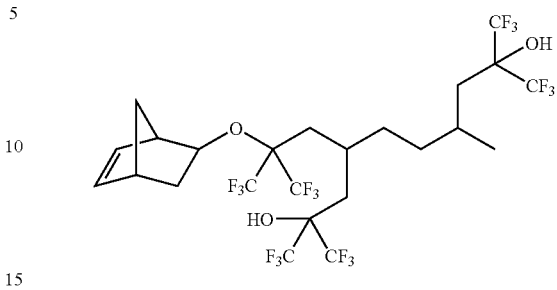

4-[bicyclo[2.2.1]hept-5-en-2-yloxy-
3,3,3-trifluoro-2-(trifluoro-
methyl)propyl]-2,9-bis(trifluoromethyl)-
1,1,1,10,10,10-hexafluoro-
7-methyldecane-2,9-diol

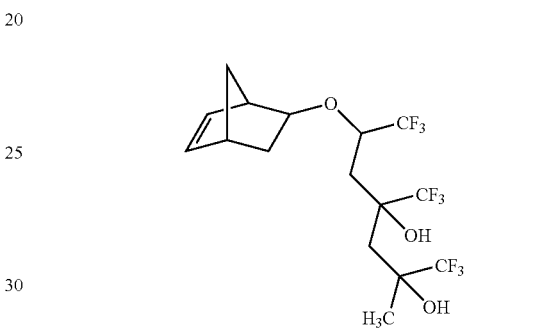

6-bicyclo[2.2.1]hept-5-en-2-yloxy-
1,1,1,7,7,7-hexafluoro-2-methyl-4-
(trifluoromethyl)heptane-2,4-diol

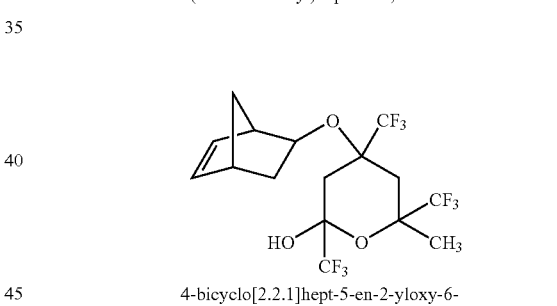

4-bicyclo[2.2.1]hept-5-en-2-yloxy-6-
methyl-2,4,6-tris(trifluoromethyl)-2H-
3,4,5,6-tetrahydropyran-2-ol In a further aspect of the present invention, there is provided a method for making a compound of the invention preferably a bridged carbocyclic compound of the above formula (I). The method comprises: combining a quantity of fluorinated alcohol with bridged carbocyclic reaction material, such as, quadricyclane, tetracyclo[4.2.0.0$^{2,8}$.0$^{5,7}$]octane, a thioquadricyclane, an oxaquadricyclane, or a substituted derivative of quadricyclane, tetracyclo[4.2.0.0$^{2,8}$.0$^{5,7}$]octane, thioquadricyclane, or oxaquadricyclane, for example, a methyl quadricyclane, a 1-trifluoromethyl quadricyclane, or a methyl thioquadricyclane, in a reaction vessel under conditions sufficient to effect a reaction to form the monomer. The fluorinated alcohol and the bridged carbocyclic reaction material may be combined with a molar ratio between from 1:1 to 3:1 of the fluorinated alcohol to bridged carbocyclic reaction material. The excess of the fluorinated alcohol is to suppress the second addition of bridged carbocyclic reaction material to the desired bridged carbocyclic compound product. In the preferred method, the reaction components are combined with a solvent, however; the use of a solvent is not mandatory. It is presently preferred to use an ether solvent, such as an alkyl ether, diethylether, di-n-butyl ether, ethylene glycol dimethyl ether; tetrahydrofuran (THF), 1,4-dioxane; or aromatic solvents such as, benzene, benzotrifluoride and toluene, or halogenated solvents, such as, Freon 113, dichloromethane, and 1,2-dichloroethane, alone or in admixtures thereof. However, other solvents such as nitriles (e. g. $CH_3CN$) or acetonitrile, alkyl alcohols, such as isopropyl alcohol, acetate solvents, such as, ethyl acetate are useful as the solvent in the method of this invention. Additionally in the preferred method, the reaction mixture is not heated nor cooled; however, heating or cooling may be done. Additionally, an acid, preferably a strong acid, such as mineral acid, e.g. sulfuric acid, or organic acid, e.g. any sulfonic acid, may be added to the reaction mixture, if desired, particularly for the purpose of speeding up the reaction. In some cases, if the pKa of the reaction mixture, particularly due to the alcohol, is less than about 11, the addition of an acid catalyst may be necessary to encourage the reaction. Acid catalysts include paratoluenesulfonic acid, trifluoromethanesulfonic acid, or solid acids, such as, sulfonic acid resins, Amberlite®IR-120(plus), and Nafion®perfluorinated ion exchange resins, and others known to those in the art.

In the preferred method, quadricyclane undergoes a ring opening addition reaction. This process may produce isomers. The reaction may produce the desired monomeric, bridged carbocyclic compound and an isomer of that compound. In the preferred process these isomers comprise a norbornene monomer (the desired monomeric, bridged carbocyclic compound) and the nortricyclane compound, referred to earlier. The isomer may be removed from the bridged carbocyclic compound monomer using any known separation technique; however, in the preferred method, the isomers are separated after the mixture of isomers undergoes a polymerization reaction, preferably a metal catalyzed addition polymerization. Metal catalysts, include but are not limited to, palladium, nickel, iron, titanium, zirconium, chromium, cobalt, rhodium, vanadium, yttrium. The preferred catalysts are palladium, nickel, iron, more preferably, palladium, and nickel. In the preferred method, the bridged carbocyclic monomer polymerizes to form the polymer of this invention. The bridged carbocyclic polymer of this invention and the isomer can then be separated, preferably the isomer is removed from the polymer by routine polymer purification steps, for example, by solvent extraction, distillation, chromatography, for example, flash or column chromatography, recrystallization, polymer precipitation, and/or trituration.

The preferred embodiments for the nortricyclane compound are the same as for the bridged carbocylic compounds comprising Structure I and II, except the nortricyclane compounds comprise a nortricyclane ring as shown in Structure III, instead of the bridged alkene-containing ring shown in Structure II. Thie nortricyclane compound can be used as a dissolution inhibitor by the incorporation of a protecting group. The protecting groups may be the same as those described below for the bridged carbocyclic compounds. A dissolution inhibitor is added to the photoresist composition. The dissolution inhibitor requires high transparency and those skilled in the art will recognize that highly fluorinated nortricyclanes will have high transparency at less than 300 nm, particularly 157 nm. The dissolution inhibitor helps to stabilize the unexposed photoresist toward base. It gives sharper line features by preventing swelling or other effects caused by the base on the insoluble resin. Use levels are from 0–30 wt %, or 5–10% of the photoresist composition.

The preferred fluorinated alcohols useful in the preferred method of making the compounds of this invention are diols, or triols although the fluorinated alcohols can comprise any number of hydroxyl groups preferably between from two to four. The preferred embodiment uses fluorinated diols to make the compounds of this invention; however, it is understood that other fluorinated alcohols are useful in the process of this invention. The preferred fluorinated alcohols include diols having fluorinated alkyl groups. The presently preferred fluorinated alcohols have symmetry. The preferred fluorinated alcohols are saturated. The preferred fluorinated alcohols have more than seven fluorines, more preferable from nine to thirty-five fluorines, most preferably from twelve to thirty fluorine atoms present on the fluorinated alcohol monomer molecule. The preferred fluorinated alcohols have one or two fluoroalkyl groups attached to the carbons that are attached to the hydroxyl groups. The preferred fluoroalkyl groups are fully fluorinated, for example, trifluoromethyl, perfluoroethyl, perfluoropropyl, and the like. The preferred fluorinated alcohols have the following structural formula:

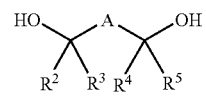

Wherein A, $R^2$, $R^3$, $R^4$, and $R^5$ are as defined above.

Examples of fluorinated alcohols useful in the process of this invention include:

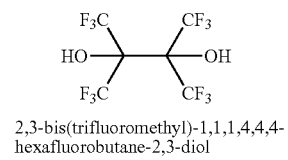

2,3-bis(trifluoromethyl)-1,1,1,4,4,4-hexafluorobutane-2,3-diol

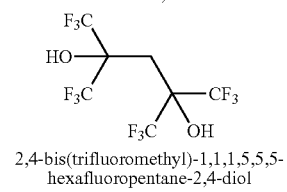

2,4-bis(trifluoromethyl)-1,1,1,5,5,5-hexafluoropentane-2,4-diol

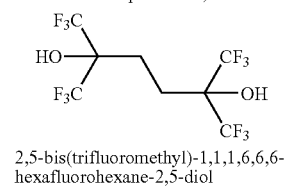

2,5-bis(trifluoromethyl)-1,1,1,6,6,6-hexafluorohexane-2,5-diol

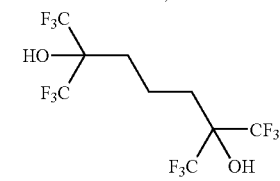

2,6-bis(trifluoromethyl)-1,1,1,7,7,7-hexafluoroheptane-2,6-diol

-continued

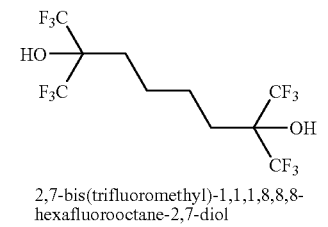

2,7-bis(trifluoromethyl)-1,1,1,8,8,8-
hexafluorooctane-2,7-diol

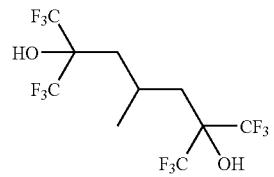

2,6-bis(trifluoromethyl)-1,1,1,7,7,7-
hexafluoro-4-methylheptane-2,6-diol

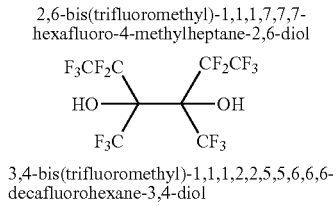

3,4-bis(trifluoromethyl)-1,1,1,2,2,5,5,6,6,6-
decafluorohexane-3,4-diol

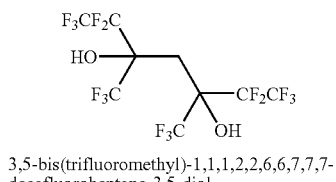

3,5-bis(trifluoromethyl)-1,1,1,2,2,6,6,7,7,7-
decafluoroheptane-3,5-diol

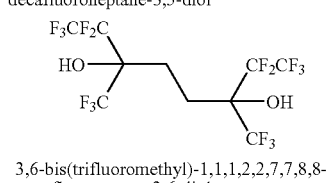

3,6-bis(trifluoromethyl)-1,1,1,2,2,7,7,8,8-
nonafluorooctane-3,6-diol

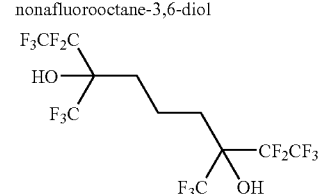

3,7-bis(trifluoromethyl)-1,1,1,2,2,8,8,9,9,9-
decafluorononane-3,7-diol

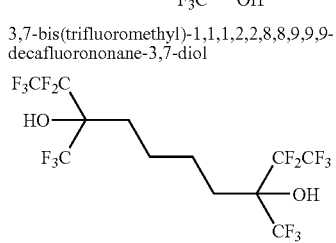

3,8-bis(trifluoromethyl)-
1,1,1,2,2,9,9,10,10,10-decafluorodecane-
3,8-diol

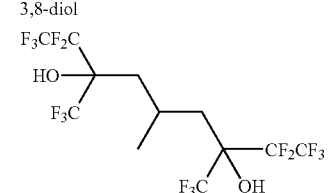

3,7-bis(trifluoromethyl)-1,1,1,2,2,8,8,9,9,9-
decafluoro-5-methylnonane-3,7-diol

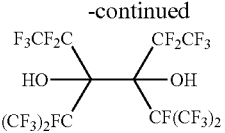

3,4-bis[1,2,2,2-tetrafluoro-1-
(trifluoromethyl)ethyl]-1,1,1,2,2,5,5,6,6,6-
decafluorohexane-3,4-diol

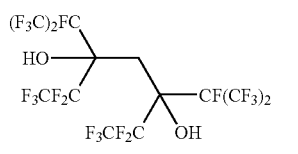

3,5-bis[1,2,2,2-tetrafluoro-1-
(trifluoromethyl)ethyl]-1,1,1,2,2,6,6,7,7,7-
decafluoroheptane-3,5-diol

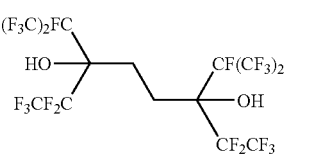

3,6-bis[1,2,2,2-tetrafluoro-1-
(trifluoromethyl)ethyl]-1,1,1,2,2,7,7,8,8,8-
decafluorooctane-3,6-diol

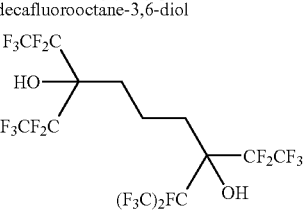

3,7-bis[1,2,2,2-tetrafluoro-1-
(trifluoromethyl)ethyl]-1,1,1,2,2,8,8,9,9,9-
decafluorononane-3,7-diol

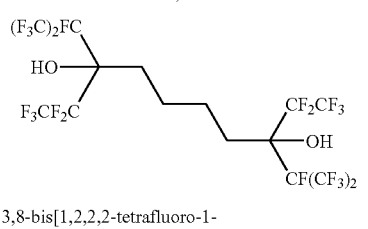

3,8-bis[1,2,2,2-tetrafluoro-1-
(trifluoromethyl)ethyl]-
1,1,1,2,2,9,9,10,10,10-decafluorodecane-3,8-diol

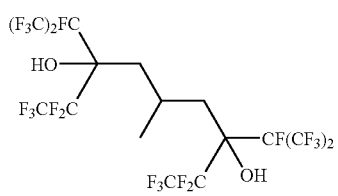

3,7-bis[1,2,2,2-tetrafluoro-1-
(trifluoromethyl)ethyl]-1,1,1,2,2,8,8,9,9,9-
decafluoro-5-methylnonane-3,7-diol

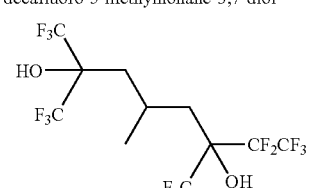

2,6-bis(trifluoromethyl)-1,1,1,7,7,8,8,8-
octafluoro-4-methyloctane-2,6-diol

-continued

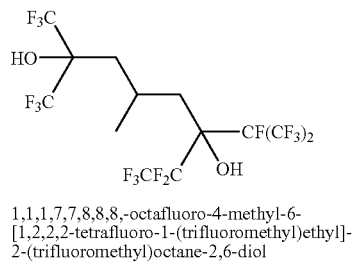

1,1,1,7,7,8,8,8,-octafluoro-4-methyl-6-
[1,2,2,2-tetrafluoro-1-(trifluoromethyl)ethyl]-
2-(trifluoromethyl)octane-2,6-diol

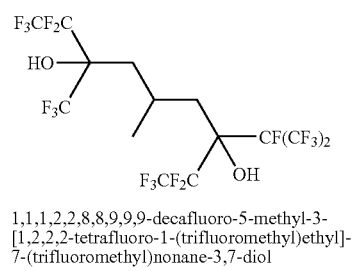

1,1,1,2,2,8,8,9,9,9-decafluoro-5-methyl-3-
[1,2,2,2-tetrafluoro-1-(trifluoromethyl)ethyl]-
7-(trifluoromethyl)nonane-3,7-diol

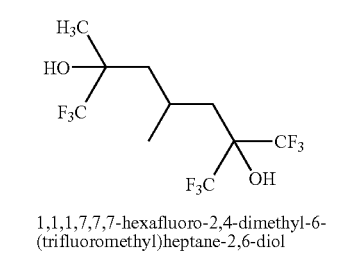

1,1,1,7,7,7-hexafluoro-2,4-dimethyl-6-
(trifluoromethyl)heptane-2,6-diol

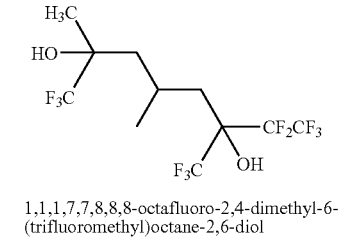

1,1,1,7,7,8,8,8-octafluoro-2,4-dimethyl-6-
(trifluoromethyl)octane-2,6-diol

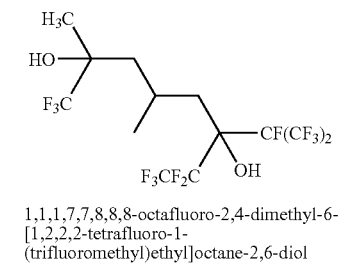

1,1,1,7,7,8,8,8-octafluoro-2,4-dimethyl-6-
[1,2,2,2-tetrafluoro-1-
(trifluoromethyl)ethyl]octane-2,6-diol

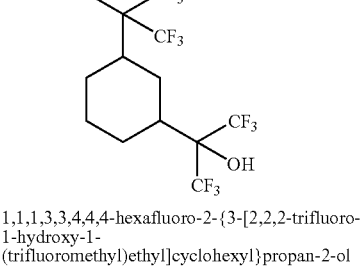

1,1,1,3,3,4,4,4-hexafluoro-2-{3-[2,2,2-trifluoro-
1-hydroxy-1-
(trifluoromethyl)ethyl]cyclohexyl}propan-2-ol -continued

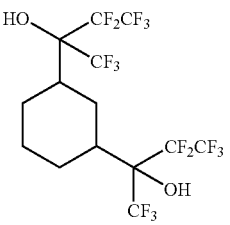

1,1,1,3,3,4,4,4-octafluoro-2-{3-[2,2,3,3,3-
pentafluoro-1-hydroxy-1-
(trifluoromethyl)propyl]cyclohexyl}butan-2-ol

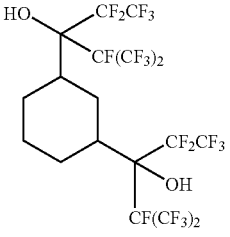

1,1,1,2,4,4,5,5,5-nonafluoro-3-(3-
{2,2,3,3,3-pentafluoro-1-hydroxy-1-
[1,2,2,2-tetrafluoro-
(trifluoromethyl)ethyl]propyl}cyclohexyl)-2-
(trifluoromethyl)pentan-3-ol

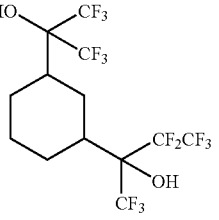

1,1,1,3,3,4,4,4-octafluoro-2-{3-[2,2,2-
trifluoro-1-hydroxy-1-
(trifluoromethyl)ethyl]cyclohexyl}butan-2-ol

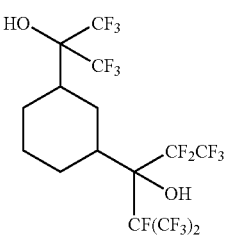

1,1,1,2,2,4,5,5,5-nonafluoro-3-{3-[2,2,2-
trifluoro-1-hydroxy-1-
(trifluoromethyl)ethyl]cyclohexyl}-4-
(trifluoromethyl)pentan-3-ol

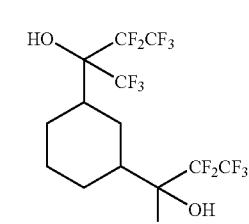

1,1,1,2,2,4,5,5,5-nonafluoro-3-{3-
[2,2,3,3,3-pentafluoro-1-hydroxy-1-
(trifluoromethyl)propyl]cyclohexyl}-4-
(trifluoromethyl)pentan-3-ol

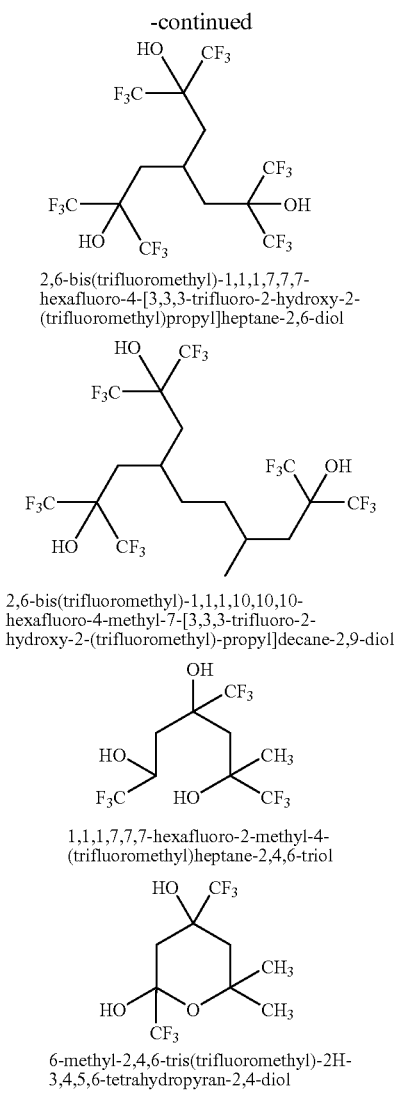

2,6-bis(trifluoromethyl)-1,1,1,7,7,7-hexafluoro-4-[3,3,3-trifluoro-2-hydroxy-2-(trifluoromethyl)propyl]heptane-2,6-diol 2,6-bis(trifluoromethyl)-1,1,1,10,10,10-hexafluoro-4-methyl-7-[3,3,3-trifluoro-2-hydroxy-2-(trifluoromethyl)-propyl]decane-2,9-diol 1,1,1,7,7,7-hexafluoro-2-methyl-4-(trifluoromethyl)heptane-2,4,6-triol 6-methyl-2,4,6-tris(trifluoromethyl)-2H-3,4,5,6-tetrahydropyran-2,4-diol The reaction of the bridged carbocyclic reaction material and the fluorinated alcohols preferably takes place in a homogeneous phase in a solvent. The combined reagents comprise 10–50 weight percent of the total mass of the reaction mixture. The reaction temperature may range from −78° C. to the boiling point of the solvent, if present, preferably 0° C. to the boiling point of the solvent, more preferably room temperature to the boiling point of the solvent. The pressure of the reaction vessel is preferably atmospheric. The reaction time for the first step may range from about 0 hours or instantaneous to about 17 days, typically from about 4 to about 12 hours.

Alternatively, some of the fluorine-containing bridged carbocyclic compounds of this invention could be made by alternate routes. Two routes that might be envisioned by those skilled in the art are: 1) addition of the mono-vinyl ether of the diols to cyclopentadiene and 2) the base-mediated addition of the diols to a norbornene halide. Both reactions are as follows:

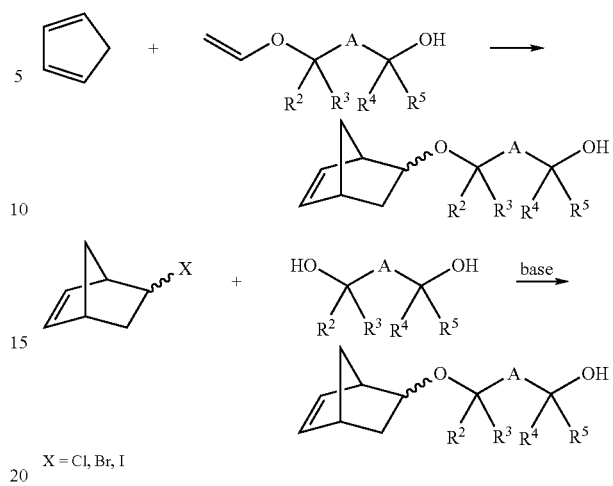

X = Cl, Br, I

The bridged carbocyclic compound of the present invention can be polymerized by itself to provide a homopolymer or with at least one other ethylenically unsaturated polymerizable monomer to provide a copolymer. The term "homopolymer" as used herein refers to polymers comprised of repeating units of one bridged carbocyclic compound, for example, a norbornene compound of the present invention. The term "copolymer" as used herein refers to polymers comprised of repeating units of the bridged carbocyclic compound of the present invention and polymerized units of at least one additional ethylenically unsaturated compound and can include, for example, random, alternating, block, star, or graft polymers. Alternatively, copolymers may comprise multiple bridged carboxylic compounds of this invention.

The bridged carbocyclic compound of the present invention may be polymerized to form a polymer by simple modifications by known methods (cf. Mathew et al, Macromolecules, 1996, Vol. 29, pp. 2755–2763.) The polymers have the following structure, formula (V):

$$\begin{array}{c} -(B')_n- \\ | \\ O \\ \diagdown \\ \phantom{O}R^2 \\ \phantom{OOO}\diagdown \phantom{a}A \\ R^3 \phantom{OO} | \\ \phantom{OOO}R^5 \\ R^4 \phantom{OO} OR^1 \end{array} \quad (V)$$

wherein (B') has the following structure, formula (VI)

$$\begin{array}{c} R^6 \quad R^7 \\ R^8 \text{—} Z \text{—} R^9 \\ R^{10} \quad R^{12} \\ R^{11} \end{array} \quad (VI)$$

In one embodiment, the polymer has the following formula:

(VII)

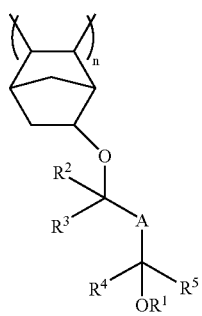

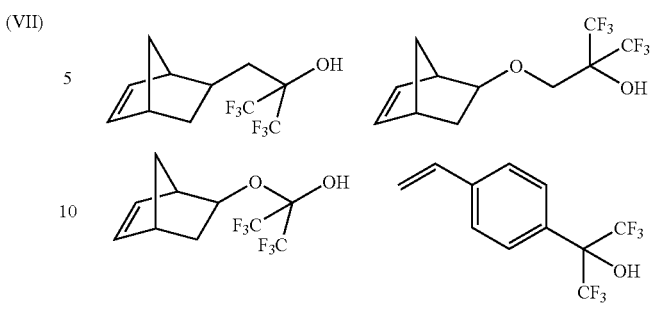

In formula V, VI, and VII $R^{1-15}$ are as defined for Formulas (I and II) above with the understanding that the olefin originally present in B is incorporated into the polymer backbone as a saturated two carbon linkage as shown in B', and n is a number ranging from 3 to 500, preferably from 5 to 150, and more preferably from 10 to 50. The polymers of formula V, VI and VII may further include polymerized units of another ethylenically unsaturated compound including other bridged carboxylic compounds to provide a copolymer.

In certain preferred embodiments of the present invention, the bridged carbocyclic compounds may be polymerized with at least one other ethylenically unsaturated monomer to form a resin or polymer. Ethylenically unsaturated monomers commonly known in the art, include those listed in The Polymer Handbook, 3rd Edition, Brandrup and Immergut, Eds., Wiley Interscience, Chapter 2, (1989). Suitable ethylenically unsaturated monomers include, for example, the $C_1$–$C_{18}$ alkyl (meth)acrylate monomers (e.g. methyl-, ethyl-, propyl-, n-butyl-, sec-butyl-, tert-butyl, pentyl-, hexyl-, isobornyl-, heptyl-, n-octyl-, 2-ethylhexyl-, decyl-, undecyl-, dodecyl-, lauryl, cetyl, and stearyl-(meth)acrylate and the like); vinyl aromatic monomers (e.g. styrene, para-hydroxystyrene, alpha-methyl styrene, para-methyl styrene, chlorostyrene, vinyl toluene, dibromostyrene, tribromostyrene, fluorostyrene, difluorostyrene, trifluorostyrene, tetrafluorostyrene, pentafluorostyrene, tetrafluorohydroxystyrene, vinyl naphthalene, isopropenyl naphthalene, divinylbenzene and the like); vinyl esters (e.g., vinyl acetate; vinyl versatate; and the like); vinyl-unsaturated carboxylic acids monomers (e.g., methacrylic acid, acrylic acid, maleic acid, itaconic acid); nitrogen-containing vinyl unsaturated monomers (e.g., acrylonitrile, methacrylonitrile, and $C_1$–$C_{18}$ alkyl (meth)acrylamides, and the like); dienes (e.g., butadiene, isoprene, and norbornadiene); ethylene, norbornene, hydroxyethyl(meth)acrylate, hydroxypropyl(meth)acrylate, and the like. The term "(meth)acrylate", as used herein, refers to esters of both methacrylate and acrylate.

Other suitable ethylenically unsaturated monomers for copolymerization with the bridged carbocyclic compound of the present invention are fluorinated olefins, such as mono-, di-, tri-, and tetrafluoroethylene. Similarly, partially and fully fluorinated derivatives of propylene, butylene, and isobutylene would be suitable co-polymers, as would fluorinated derivatives of maleic anhydride, fluoro-(meth)acrylates (vinyl substituted), and fluoro-methacrylates (methyl substituted), and fluorovinyl ethers. Other usable monomers are shown below:

A particularly useful embodiment would be the utilization of co-monomers that contain acid-labile groups to facilitate the development of these materials when used in photoresists. The co-monomer structure can be generally described as PF-O-PG, where PF is a polymerizable fragment that influences the oxygen such that PF-OH would be acidic ($pK_a<12$) and PG is an acid-labile protecting group that can be removed under the influence of acid (i.e. from a photoacid generator). PF-OH are the compounds of this invention and include the compounds of Formula (I). Suitable examples of PF would be (meth)acryloyl groups as described above, and suitably fluoro-substituted alkyl groups (also described above). Examples of PGs would be tertiary alkoxy groups (for when PF-O-PG is an ester), tert-alkoxycarbonyl groups, alkoxy methyl groups of type —OCHROR' (including cyclic derivatives where R and R' are joined together in a ring). Specific individual monomers of type PF-O-PG are shown below:

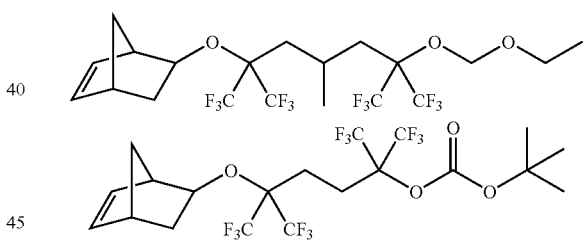

Alternatively the bridged carbocyclic monomers of this invention can be polymerized with ethylenically unsaturated monomers containing protecting groups. Examples of such monomers having protecting groups and the PF-O-PG structures are as follows:

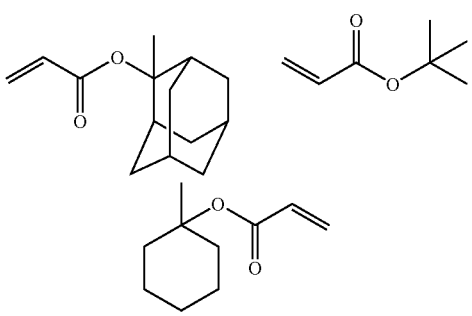

-continued

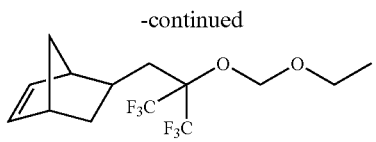

It is also possible to have the protecting group incorporated in such as fashion so as to be non-fragmenting (see below):

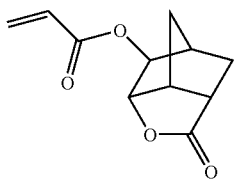

A polymer may be prepared using the bridged carbocyclic compound or compounds of this invention as a monomer or monomers, and optionally at least one other ethylenically unsaturated monomer, using a typical polymerization process such as bulk polymerization, solution polymerization, batch polymerization, suspension polymerization or emulsion polymerization. The polymerization reaction can be initiated by a free-radical polymerization initiator or a metal catalyst. Any initiator or catalyst is suitable for use in the present invention as long as it catalyzes the polymerization of the double bond without substantially opening the ring of the bridged carbocyclic compound monomer. In general, the polymerization reaction may be conducted by combining one or more types of monomers to form a reaction mixture, adding a metal catalyst or polymerization initiator to the reaction mixture, and effecting polymerization reaction while heating or cooling the system if necessary. The time and temperature conditions for the polymerization reaction to occur depend upon a variety of factors such as whether solvent is used within the reaction mixture, whether a metal catalyst or polymerization initiator is used, trigger means (i.e., light, heat, radiation, plasma, etc.), polymerization conditions (i.e., temperature, pressure, solvent, concentration, and additives), and the like.

In embodiments where a free-radical polymerization initiator is used, suitable initiators include, but are not limited to, Vazo initiators such as 2, 2' azobis(isobutyronitrile) (AIBN), hydrogen peroxide, tert-butyl hydroperoxide, sodium persulfate, potassium persulfate, lithium persulfate; and the like. In alternative embodiments, a metal polymerization catalyst may be used. Suitable metal polymerization catalysts include, but are not limited to, palladium, nickel, iron, titanium, zirconium, chromium, cobalt, rhodium, vanadium, yttrium. The preferred catalysts are palladium, nickel, iron, more preferably, palladium, and nickel.

The polymer of the present invention preferably has a number average molecular weight that ranges from 500 to 100,000, more preferably from 500 to 150,000, and most preferably from 750 to 40,000, and ideally 1,000 to 20,000 as determined by gel chromatography.

The molecular weight of the polymers of this invention can be modified by the addition of a molecular weight modifier to the reaction mixture used to form the polymers. We found ethyl acetate to be a particularly effective modifier; however other materials that would be useful include methyl propionate, butyl lactate, and propylene glycol methyl ether acetate (PGMEA). The preferred amount of molecular weight modifier to add to the reaction mixture is from 0.5 to 9 times or from 1 to 3 times the moles of polymerizable monomer present in the reaction mixture; however the optimum amount of molecular weight modifier to add can be determined by experimentation depending up the molecular weight desired for each reaction mixture. Example 22 below shows the effect of the addition of molecular weight monomer on the polymerization of a bridged carbocyclane compound of this invention. It is believed that the molecular weight modifiers added to a reaction mixture would be useful to control the molecular weight of polymers comprising any bridged carbocyclic compounds.

A photoresist composition may be formulated using the polymer resulting from polymerization of the bridged carbocyclic compound of the present invention and optionally one or more ethylenically unsaturated monomers. A typical photoresist composition comprises a polymer, a photoactive compound, which may be incorporated into the polymer, optionally a crosslinker, optionally a basic compound, optionally a dissolution inhibitor, and optionally other additives such as, but not limited to, anti-striation agents, plasticizers, speed enhancers, fillers, dyes, and the like within a solvent medium. Typically, the solids content of the photoresist composition varies from about 5 to about 35 percent by weight, based on the total weight of the composition. The polymer and photoactive component should be present in amounts sufficient to provide a film coating layer and formation of good quality latent and relief images. Other optional additives will be present in relatively minor concentrations in the photoresist composition.

The photoactive compound is typically added to the photoresist composition in an amount sufficient to generate a latent image in a coating layer of resist material upon exposure to activating radiation. The photoactive compounds useful in the present invention are typically photoacid or photobase generators, and are preferably photoacid generators ("PAG"). The photoacid generators useful in the present invention are any compound which liberates acid upon exposure to light, typically at a wavelength of 300 nanometers or less. Suitable photoacid generators include halogenated triazines, onium salts, sulfonated esters and halogenated sulfonyloxy dicarboximides. When the photoactive compound is a photoacid generator, the amount is typically in the range of 0.1 to 10 percent by weight, based on the weight of the resin, and preferably 1 to 8 percent by weight. It will be appreciated by those skilled in that art that more than one photoacid generator may be used advantageously in the photoresist compositions of the present invention.

Onium salts with weakly nucleophilic anions are particularly suitable for use as photoacid generators in the present invention. Examples of such anions are the halogen complex anions of divalent to heptavalent metals or non-metals, for example, antimony, tin, iron, bismuth, aluminum, gallium, indium, titanium, zirconium, scandium, chromium, hafnium, copper, boron, phosphorus and arsenic. Examples of suitable onium salts include, but are not limited to: diaryl-diazonium salts and onium salts of group VA and B, IIA and B and I of the Periodic Table, for example, halonium salts, quaternary ammonium, phosphonium and arsonium salts, aromatic sulfonium salts and sulfoxonium salts or selenium salts. Examples of suitable onium salts are disclosed in U.S. Pat. Nos. 4,442,197; 4,603,101; and 4,624,912, all incorporated herein by reference. The sulfonated esters useful as photoacid generators in the present invention include sulfonyloxy ketones. Suitable sulfonated esters include, but are not limited to: benzoin tosylate, t-butylphenyl alpha-(p-toluenesulfonyloxy)-acetate, and t-butyl alpha-(p-toluenesulfonyloxy)acetate. Such sulfonated esters are disclosed in the Journal of Photopolymer Science and Technology, vol. 4, No. 3,337-340 (1991), incorporated herein by reference.

The photoresist compositions of the present invention may be readily prepared by those skilled in the art. For example, a photoresist composition of the invention can be prepared by dissolving the components of the photoresist composition in a suitable solvent. Such suitable solvents include, but are not limited to: ethyl lactate, ethylene glycol monomethyl ether, ethylene glycol monomethyl ether acetate, propylene glycol monomethyl ether, propylene glycol monomethyl ether acetate, 3-ethoxyethyl propionate, 2-heptanone, and mixtures thereof.

Such photoresist compositions may be applied to a substrate by any known means, such as spinning, dipping, roller coating and the like. When the compositions are applied by spin coating, the solids content of the coating solution can be adjusted to provide a desired film thickness based upon the specific spinning equipment utilized, the viscosity of the solution, the speed of the spinner and the amount of time allowed for spinning.

Photoresist compositions including the polymers of the present invention are useful in all applications where photoresists are typically used. For example, the compositions may be applied over silicon wafers or silicon wafers coated with silicon dioxide for the production of microprocessors and other integrated circuit components. Aluminum-aluminum oxide, gallium arsenide, ceramic, quartz, copper, glass, indium tin oxide (ITO), and indium tin oxide (ITO) coated glass, and the like are also suitable employed as substrates for the photoresist compositions of the invention.

Once the photoresist composition is coated on a substrate surface, it is dried by heating to remove any solvent. It is preferably dried until the coating is tack free. Thereafter, it is imaged through a mask in a conventional manner. The exposure is sufficient to effectively activate the photoacid component of the photoresist composition to produce a patterned image in the resist coating layer, and more specifically, the exposure energy typically ranges from about 1 to 100 mJ/cm$^2$, dependent upon the exposure tool and the components of the photoresist composition.

The photoresist compositions of the present invention are preferably activated by a short exposure wavelength, particularly a sub-300 nm, such as UV, and more preferably a sub-200 nm exposure wavelength. Particularly preferred wavelengths include 248, 193, and 157 nm. However, the photoresist compositions of the present invention may be used at higher wavelengths, such as, but not limited to, visible, e-beam and x-ray.

The invention will be illustrated in more detail with reference to the following examples, but it should be understood that the present invention is not deemed to be limited thereto. The examples show the methods of making bridged carbocyclic compounds, nortricyclane compounds, polymers of this invention, and photoresist compositions, as well as the methods for making the reaction materials for making those compounds. The gas chromatography mass spectroscopy (GC/MS Spectra) for the examples were performed on a Hewlett Packard 6890 Series GC and 5973 series mass selective detector with a 30 meter HP-5 capillary column. Vacuum ultraviolet variable angle spectroscopic ellipsometery (VUV-VASE), measurements were performed by J. A. Woollam Co., Inc., Lincoln, Nebr. gc/fid is gas chromatography with flame ionization. GPC is gel permeation chromatography. The percentages and ratios in the examples are based on area % as determined by gc/fd analysis.

EXAMPLES

Example 1

Reaction of 2,5-bis(trifluoromethyl)-1,1,1,6,6,6-hexafluoro-hexane-2,5-diol (Compound 1 with quadricyclane 2,5-bis(trifluoromethyl)-1,1,1,6,6,6-hexafluoro-3-hexyne-2,5-diol was prepared as described by Knunyants, et al., Bull. Acad. Sci. USSR (English translation, 1960, pp 647–653). The acetylenic diol (68 grams) was placed in a 1 liter pressure vessel with 6.8 g 5% platinum on carbon (50% water wet, Aldrich) and 6.7 g 4% rhodium on alumina (Engelhard) and 500 mL of 2-propanol. The reactor was purged with nitrogen and then hydrogen and then pressurized with hydrogen and heated to 120° C. and the hydrogen pressure adjusted to 1200 psig. The reaction mixture was stirred at 1200 psig and 120° C. for 4 hours. The reactor was cooled, vented, and the contents were concentrated in vacuo to give 27.7 g of white solid, Compound 1, whose structure was verified by $^{13}$C nmr and GC/MS. This material was used without further purification for the reaction with quadricyclane.

To 3.86 grams of 1,2-dichloroethane in a glass tube were added 10.1 grams of Compound 1 and 2.6 grams of quadricyclane. The tube was sealed and heated to 70° C. for 5 hours. The cooled contents of the glass vessel were purified by flash chromatography on 180 grams of silica gel (230–400 mesh) using 50% dichloromethane/hexanes as eluant. The combined eluants were concentrated in vacuo to give 11.1 grams of a 99% pure mixture, as determined by gas chromatography with flame ionization detector (gc-fid), of the ethers 5-(bicyclo[2.2.1]hept-5-en-2-yloxy-2,5-bis(trifluoromethyl)-1,1,1,6,6,6-hexafluorohexan-2-ol and 2,5-bis(trifluoromethyl)-1,1,1,6,6,6-hexafluoro-5-tricyclo[2.2.1.0$^{2,6}$]hept-3-yloxyhexan-2-ol (Compounds 2 and 3, respectively) in a 70:30 ratio. This material was used as the mixture in the polymerization in Example 5.

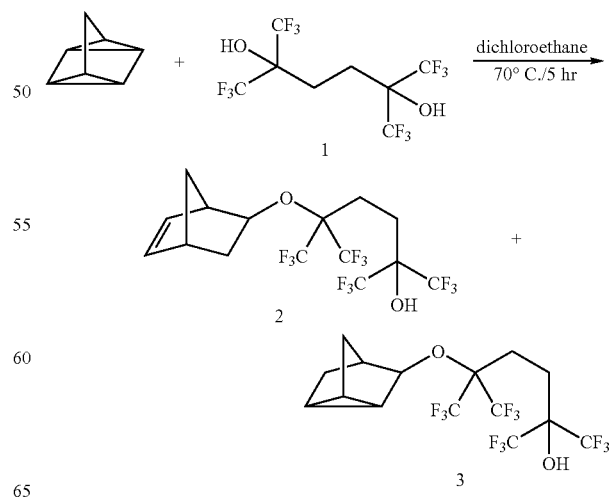

Example 2

Reaction of 2,3-bis(trifluoromethyl)-1,1,1,4,4,4-hexafluorobutanane-2,3-diol (Compound 4) with quadricyclane To 23 grams of tetrahydrofuran in a glass tube were added 12.2 grams of 2,3-bis(trifluoromethyl)-1,1,1,4,4,4-hexafluorobutanane-2,3-diol (Compound 4) purchased from Matrix Scientific, Columbia, S.C., USA, and 5.9 grams of quadricyclane. The tube was sealed and heated to 65° C. for 4 hours. The cooled contents of the glass vessel were concentrated in vacuo and then distilled at 52–58° C. and 0.4 torr to give 8.63 grams of a clear colorless liquid which was a 97.7% pure (gc/fid) mixture of 3-(bicyclo[2.2.1]hept-5-en-2-yloxy-2,3-bis(trifluoromethyl)-1,1,1,4,4,4-hexafluorobutanol-2-ol, and 2,5-bis(trifluoromethyl)-1,1,1,6,6,6-hexafluoro-5-tricyclo[2.2.1.0$^{2,6}$]hept-3-yloxyhexan-2-ol (Compounds 5 and 6 respectively) in an 80:20 ratio.

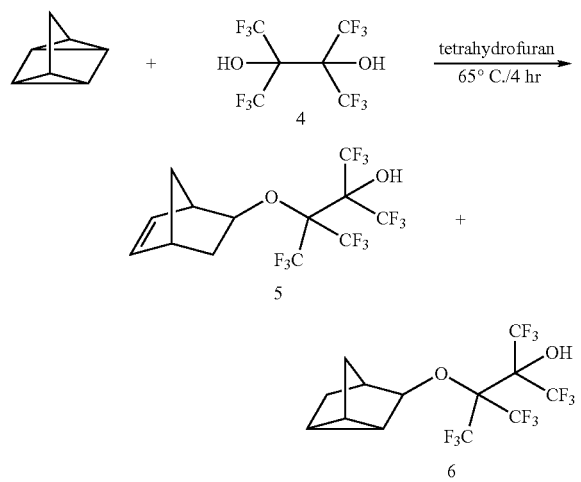

Example 3

Reaction of 2,6-bis(trifluoromethyl)-1,1,1,7,7,7-hexafluoro-4-methyl-2,6-heptanediol (Compound 7 with quadricyclane The method described by Urry et al. (J. Org. Chem. 1968, vol. 33, pp 2302–2310) was used to obtain the mixture of olefins shown as reactants below.

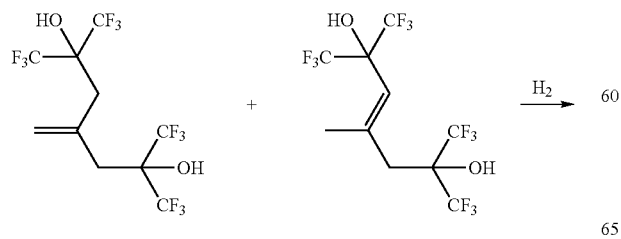

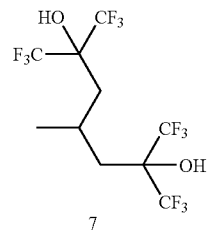

The mixed olefin product was sublimed (80° C., 0.01–0.05 torr) and the purified mixture (8.5 grams) was placed in a 300 mL pressure vessel with 3.2 grams 5% Platinum on carbon (60% water wet, Johnson Matthey) and 3.7 grams 4% rhodium on alumina (Engelhard), along with 145 milliliter of 2-propanol. The vessel was pressurized and heated and the reaction was allowed to proceed with stirring at 1100 psig and 120° C. for 46 hours. At the end of this time, the vessel was cooled, vented and the reactor contents were concentrated in vacuo, leaving behind 2,6-bis(trifluoromethyl)-1,1,1,7,7,7-hexafluoro-4-methyl-2,6-heptanediol (Compound 7) as a liquid (9.0 grams). This was used without further purification.

To 20 milliliters of tetrahydrofuran in a glass tube were added 19.6 grams of Compound 7 and 4.1 grams of quadricyclane. The tube was sealed and heated to 65° C. for 11 days. The cooled contents of the glass vessel were concentrated in vacuo and then distilled at 70–93° C. and 0.4 torr to give 15.1 grams of a clear colorless liquid which was a 98.4% pure (gc/fid) mixture of 6-bicyclo[2.2.1]hept-5-en-2-yloxy-2,6-bis(trifluoromethyl)-1,1,1,7,7,7-hexafluoro4-methylheptan-2-ol, and 2,6-bis(trifluoromethyl)-1,1,1,7,7,7-hexafluoro-4-methyl-6-tricyclo[2.2.1.0$^{2,6}$]hept-3-yloxyheptan-2-ol (Compounds 8, and 9, respectively) and unreacted Compound 7 in a 69.2:13.1:17.5 ratio.

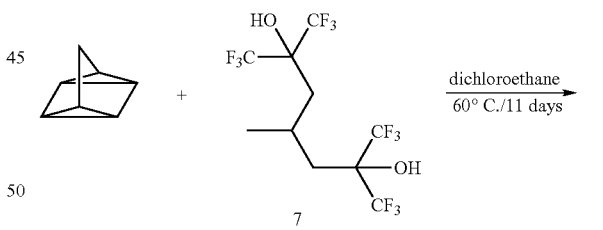

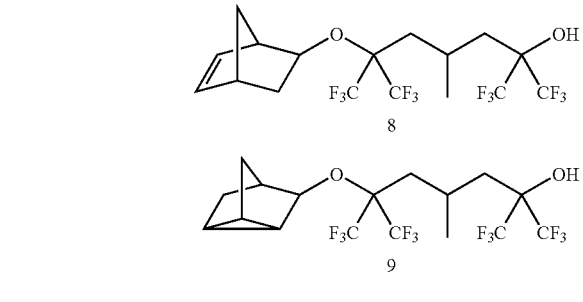

Example 4

Reaction of 1,1,1,3,3,3-hexafluoro-2-{3-[2,2,2-trifluoro-1-hydroxy-1-(trifluoromethyl)ethyl]cyclohexyl}propan-2-ol (Compound 10) with quadricyclane To 9.7 grams of dichloroethane in a glass tube were added 17.6 grams of 1,1,1,3,3,3-hexafluoro-2-{3-[2,2,2-trifluoro-1-hydroxy-1-(trifluoromethyl)ethyl]cyclohexyl}propan-2-ol (Compound 10) and 4.54 grams of quadricyclane. Compound 10 can be prepared as described for the mixture of 1,3- and 1,4-isomers by Maruno et al., Macromolecules 1996, vol. 29, pp 2006–2010. The tube was sealed and heated to 60° C. for 17 days. The cooled contents of the glass vessel were concentrated in vacuo and then distilled at 108–125° C. and 0.8 torr to give 15.1 grams of a clear colorless liquid which was a 98.4% pure (gc-fid) mixture of 2-{3-[1-(bicyclo[2.2.1]hept-5-en-2-yloxy-2,2,2-trifluoro-1-(trifluoromethyl)ethyl]cyclohexyl}-1,1,1,3,3,3-hexafluoropropan-2-ol and the nortricyclane compound isomer (Compounds 11 and 12, respectively) in an 34:66 ratio.

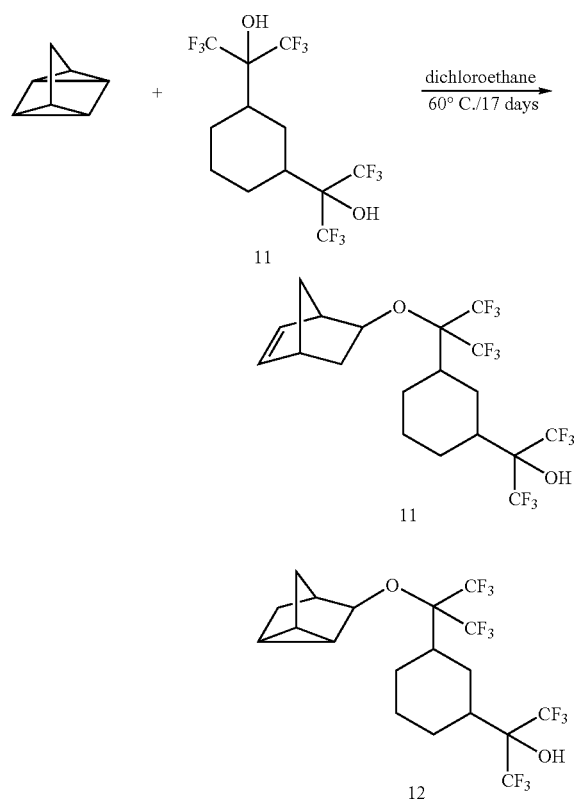

Example 5

Reaction of 6-methyl-2,4,6-tris(trifluoromethyl)-2H-3,4,5,6-tetrahydropyran-2,4-diol (Compound 13) with quadricyclane To 12.0 g of 1,2-dichloroethane in a glass tube were added 7.5 g of Compound 13, 2.6 g of quadricyclane and 0.1 g of p-toluenesulfonic acid (TsOH). The tube was sealed and heated to 70° C. for 5 days. The cooled contents of the glass vessel were extracted with aqueous sodium bicarbonate and then saturated aqueous sodium chloride and then dried over sodium sulfate and concentrated in vacuo and then distilled at 52–62° C. and 0.05 torr to give 9.37 g of a clear viscous liquid which was a 90.8% pure (gc-fid) mixture of 4-bicyclo[2.2.1]hept-5-en-2-yloxy-6-methyl-2,4,6-tris(trifluoromethyl)-2H-3,4,5,6-tetrahydropyran-2-ol and 6-methyl-4-tricyclo[2.2.1.0$^{2,6}$]hept-3-yloxy-2,4,6-tris(trifluoromethyl)-2H-3,4,5,6-tetrahydropyran-2-ol (Compounds 14 and 15, respectively) in a 55:45 ratio.

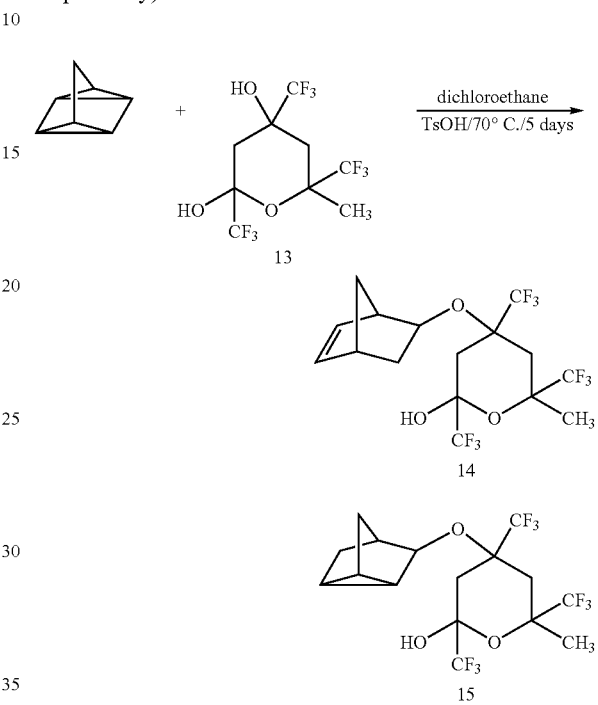

Comparative Example

The process of Example 5 was repeated, except that the p-toluenesulfonic acid was omitted. No reaction occurred.

Example 6

Preparation of 1,1,1,7,7,7-hexafluoro-2-methyl-4-(trifluoromethyl)heptane-2,4,6-triol (Compound 16)

Into a 300 mL stainless steel (ss) autoclave was placed 22.8 g of Compound 13, 4.5 g of 5% Pt on C (50% water wet), 4.8 g of 4% Rh on alumina, and 150 mL of isopropyl alcohol. The autoclave was purged with nitrogen then hydrogen and then heated to 100° C. and the hydrogen pressure adjusted to 1100 psig with hydrogen and allowed to react for 143 hours. The reactor was then cooled, vented, and discharged through an inline filter. The filtrate was concentrated in vacuo to give 18.4 g of a clear liquid which was 98.4% pure Compound 16 by gc-fid.

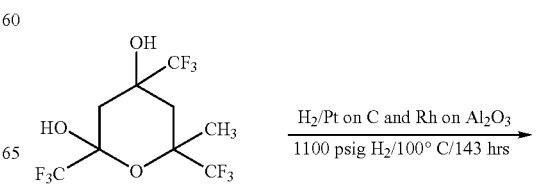

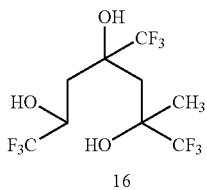

16

Example 7

Reaction of 1,1,1,7,7,7-hexafluoro-2-methyl-4-(trifluoromethyl)heptane-2,4,6-triol (Compound 16) with quadricyclane To 10.1 g of 1,2-dichloroethane in a glass tube were added 10.3 g of Compound 1, 3.3 g of quadricyclane and 0.1 g of p-toluenesulfonic acid. The tube was sealed and heated to 70° C. for 5 days. The cooled contents of the glass vessel were extracted with aqueous sodium bicarbonate and then saturated aqueous sodium chloride and then dried over sodium sulfate and concentrated in vacuo and then chromatographed on silica gel eluting with methylene chloride to give 4.53 g of a clear, viscous light yellow oil which was a 96.4% pure (gc-fid) mixture of 6-bicyclo[2.2.1]hept-5-en-2-yloxy-1,1,1,7,7,7-hexafluoro-2-methyl-4-(trifluoromethyl) heptane-2,4-diol and 1,1,1,7,7,7-hexafluoro-2-methyl-6-tricyclo[2.2.1.0$^{2,6}$]hept-3-yloxy-4-(trifluoromethyl)heptane-2, 4-diol (Compounds 17 and 18, respectively) in a 53:47 ratio.

Example 8

3:1 Reaction product of hexafluoroacetone (HFA) and 2,5-dimethyl-1,6-hexadiene and hydrogenation thereof Into a 300 mL ss autoclave was charged 22.26 g of 2,5-dimethyl-1,5-hexadiene and 134.14 g of hexafluoroacetone. The reactants were heated to 165° C. for 48 hours and 119 of light yellow oil consisting of bis, tris and tetra-HFA adducts were obtained. The bulk of the bis adduct was removed from 68.2 g of this material by removing 48.2 g by Kugelrohr distillation at 87–97° C. and 0.5 torr. Continuing the Kugelrohr distillation at 110–127° C. and 0.4 torr gave 16.3 g of material which was hydrogenated as follows. Into a 1 L ss autoclave was placed 16.3 g of the diolefin mixture, 3.7 g of 5% Pt on C (50% water wet), 3.6 g of 4% Rh on alumina, and 500 mL of isopropyl alcohol. The autoclave was purged with nitrogen then hydrogen and heated to 120° C. and 1100 psig hydrogen for 45 hours. The reactor was then cooled, vented, and discharged through an inline filter. The filtrate was concentrated in vacuo to give 12.8 g of a clear viscous liquid which was a mixture of 2,9-bis(trifluoromethyl)-1,1,1,10,10,10-hexafluoro4,7-dimethyldecane-2, 9-diol; 2,9-bis(trifluoromethyl)-1,1,1,10,10,10-hexafluoro-4-methyl-7-[3,3,3-trifluoro-2-hydroxy-2-(trifluoromethyl) propyl]decane-2,9-diol; and 4,7-bis[3,3,3-trifluoro-2-hydroxy-2-(trifluoromethyl)propyl]-2,9-bis (trifluoromethyl)-1,1,1,10,10,10-hexafluorodecane-2,9-diol (Compounds 19, 20, and 21, respectively) in a ratio of 5 4.0:90.9:5.1 by gc-fid area %.

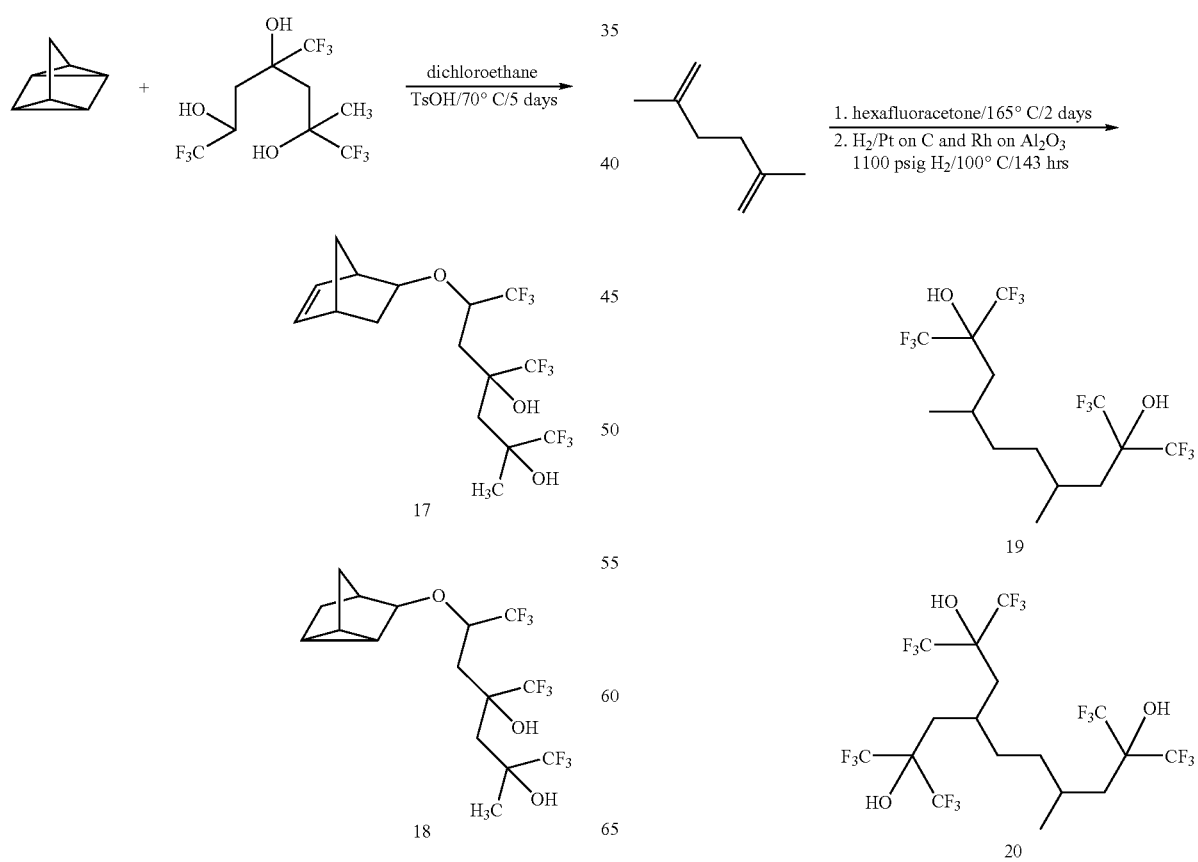

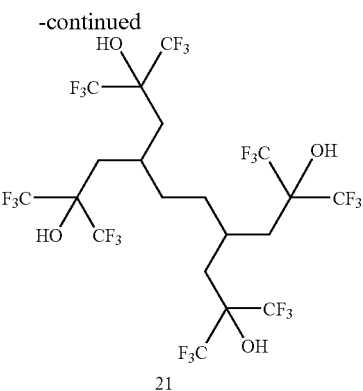

21

Example 9

Reaction of mixture from Example 8 with quadricyclane

To 5.1 g of 1,2-dichloroethane in a glass tube were added 4.84 g of the above described mixture of Compounds 19, 20, and 21, and 0.50 g of quadricyclane. The tube was sealed and heated to 70° C. for 40 min. The crude product was concentrated in vacuo and chromatographed on silica gel eluted with hexane/methylene chloride to give 1.64 g of a mixture of the two norbornenes: 4-[5-bicyclo[2.2.1]hept-5-en-2-yloxy-6,6,6-trifluoro-3-methyl-5-(trifluoromethyl)hexyl]-2,6-bis(trifluoromethyl)-1,1,1,7,7,7-hexafluoroheptane-2,6-diol and 7-[2-bicyclo[2.2.1]hept-5-en-2-yloxy-3,3,3-trifluoro-2-(trifluoromethyl)propyl]-2,9-bis(trifluoromethyl)-1,1,1,10,10,10-hexafluoro-4-methyldecane-2,9-diol and the two nortricyclanes compounds: 7-[2-bicyclo[2.2.1]hept-5-en-2-yloxy-3,3,3-trifluoro-2-(trifluoromethyl)propyl]-2,9-bis(trifluoromethyl)-1,1,1,10,10,10-hexafluoro-4-methyldecane-2,9-diol and 2,9-bis(trifluoromethyl)-1,1,1,10,10,10-hexafluoro-4-methyl-7-[3,3,3-trifluoro-2-tricyclo[2.2.1.0<2,6>]hept-3-yloxy-2-(trifluoromethyl)propyl]decane-2,9-diol (Compounds 22 and 23 (norbornenes) and Compounds 24 and 25 (nortricyclane compounds)) with a combined norbornene:nortricyclane ratio of 71:29 by gc-fid.

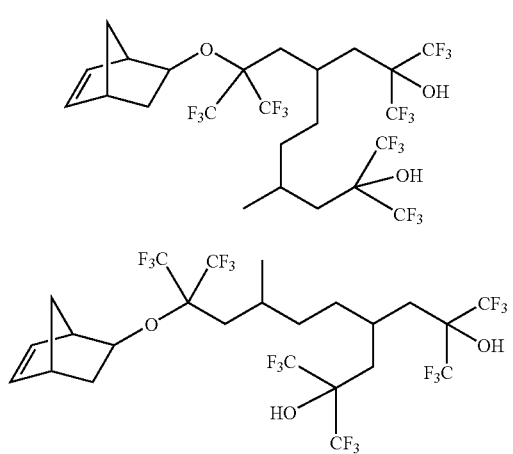

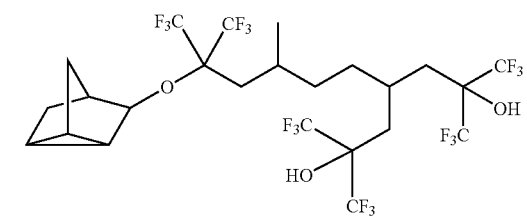

A later eluting material Compound 29 was also obtained, which was found to be the reaction product of Compound 21 and quadricyclane.

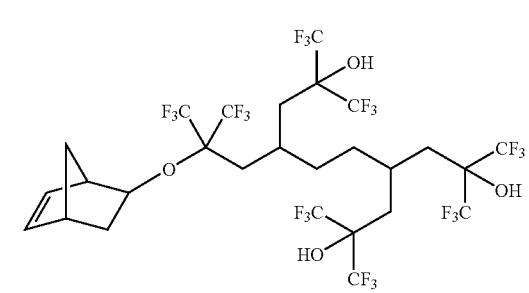

Example 10

Preparation of 2,6-bis(trifluoromethyl)-1,1,1,7,7,7-hexafluoro-4-[3,3,3-trifluoro-2-hydroxy-2-(trifluoromethyl)propyl]heptane-2,6-diol (Compound 26)

Into a 1 L ss autoclave was placed 35.7 g of the olefin (obtained as described by Urry et al. (J. Org. Chem. 1968, vol. 33, pp 2302–2310), 5.4 g of 5% Pt on C (50% water wet), 5.4 g of 4% Rh on alumina, and 500 mL of isopropyl alcohol. The autoclave was purged with nitrogen then hydrogen and then heated to 120° C. and the hydrogen pressure adjusted to 1200 psig with hydrogen and allowed to react for 7 days. The reactor was then cooled, vented, and discharged through an inline filter. The filtrate was concentrated in vacuo to give 30.0 g of a white solid which was 94.5% pure Compound 26 by gc-fid.

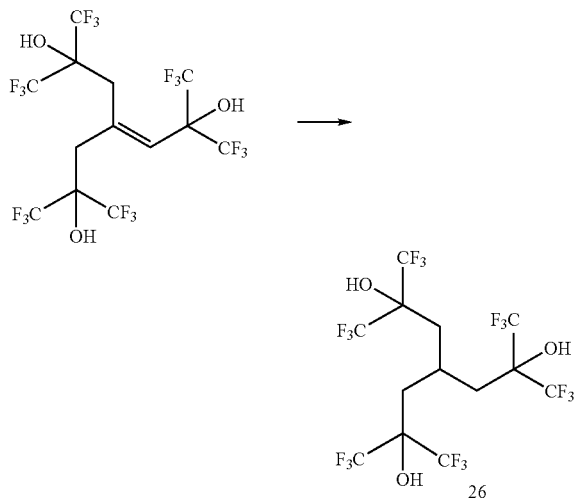

Example 11

Reaction of 2,6-bis(trifluoromethyl)-1,1,1,7,7,7-hexafluoro-4-[3,3,3-trifluoro-2-hydroxy-2-(trifluoromethyl)propyl]heptane-2,6-diol (Compound 26) with quadricyclane To 15.0 g of 1,2-dichloroethane in a glass tube were added 12.9 g of Compound 26 and 1.2 g of quadricyclane. The tube was sealed and heated to 55° C. for 40 min. The crude product was concentrated in vacuo and chromatographed on silica gel eluted with hexanes/methylene chloride to give 3.93 g of a mixture of 4-[2-bicyclo[2.2.1]hept-5-en-2-yloxy-3,3,3-trifluoro-2-(trifluoromethyl)propyl]-2,6-bis(trifluoromethyl)-1,1,1,7,7,7-hexafluoroheptane-2,6-diol and 2,6-bis(trifluoromethyl)-1,1,1,7,7,7-hexafluoro-4-[3,3,3-trifluoro-2-tricyclo[2.2.1.0$^{2,6}$]hept-3-yloxy-2-(trifluoromethyl)propyl]heptane-2,6-diol (Compounds 27 and 28, respectively) in a 63:37 ratio.

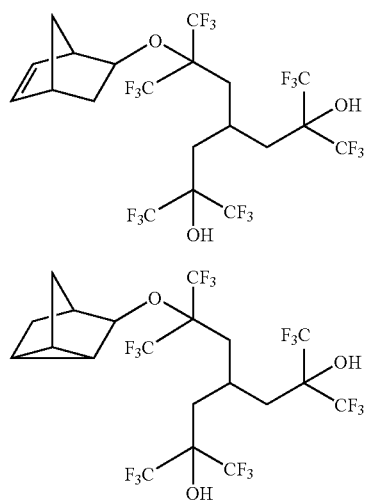

Example 12

Polymerization of monomer Compound 2

This metal catalyzed polymerization was conducted in a nitrogen atmosphere. A 70:30 mixture of Compounds 2 and 3 (5.64 g total=8.7×10$^{-3}$ mol of polymerizable monomer Compound 2) was degassed under vacuum and placed under a nitrogen atmosphere.

A sample vial was charged with 31.89 mg (8.72×10$^{-5}$ moles) of (η$^3$-allyl) palladium chloride dimer, 60.15 mg (1.75×10$^{-4}$ moles) of silver hexafluoroantimonate, and 4 mL of chlorobenzene. The catalyst mixture was stirred for 20 minutes at 20° C. The silver chloride formed was filtered off with a syringe filter (0.2 micrometers). The clear yellow solution was added to the degassed mixture of monomer Compound 2 and isomer Compound 3 (nortricyclane compound). Within five minutes the solution became cloudy with some white particulates in the yellow solution. In ≦2 hours the solution had solidified to a whitish gel. After about 19 hours the contents of the vial were removed as one semi-rigid solid. This solid was broken into small pieces and dissolved in 25.5 grams of tetrahydrofuran. A small portion of the solution was analyzed by gc-fid. The initial ratio of adducts was 70:30 and the final ratio was 1:77 indicating that conversion of the polymerizable monomer was 99%. The polymer was precipitated from the tetrahydrofuran solution by adding it to 1000 mL of hexanes to give 3.78 grams of a stringy white solid which was dried at 50° C. and 1 millibar to a constant weight of 3.62 grams of a fibrous white solid. The final yield of this polymerization was 95%.

As previously stated, compound 3 does not react during the polymerization, and can be isolated from the remaining solution by standard isolation and purification procedures, such as recrystallization, distillation, or preparative scale chromatography.

The molecular weight (MW) as determined by gel permeation chromatography relative to polystyrene molecular weight reference standard (GPC relative to PS standards) was number average molecular weight ($M_n$) of 133,000 and weight average molecular weight ($M_w$) of 440,500.

Example 13

Polymerization of monomer Compound 5

This metal catalyzed polymerization was conducted in a nitrogen atmosphere. A 46:54 mixture of Compounds 5 and 6 (6.04 grams total=6.5×10$^{-3}$ mol of polymerizable monomer Compound 5) was degassed under vacuum and placed under a nitrogen atmosphere.

A sample vial was charged with 23.92 mg (6.5×10$^{-5}$ mol) of (η$^3$-allyl) palladium chloride dimer, 45.11 mg (1.31×10$^{-4}$ mol) of silver hexafluoroantimonate, and 3 mL of chlorobenzene. The catalyst mixture was stirred for 20 minutes at 20° C. The silver chloride formed was filtered off with a syringe filter (0.2 micrometers). The clear yellow catalyst solution was added to the degassed mixture of monomer Compounds 5 and isomer Compound 6 (nortricyclane compound) to give a clear yellow solution. After 20 hours the clear yellow solution had become very viscous but had not gelled. A small portion of the solution was analyzed by gc/fid. The initial ratio of adducts were 46:54 and the final ratio was 16.6:83.4 indicating that conversion of the polymerizable monomer was 76.6%. The viscosity decreased dramatically with the addition of 4.88 grams of ethyl acetate and this solution was added to 200 mL of hexanes. A white precipitate formed and was filtered from the liquid. The polymer was dried at 50° C. and 1 millibar to constant weight to give 2.1 grams of a white powder. The final yield on this polymerization was 75.5%. The MW as determined by GPC relative to PS standards was $M_n$=19,000 and $M_w$=40,000.

Example 14

Polymerization of monomer Compound 8

This metal catalyzed polymerization was conducted in a nitrogen atmosphere. A 69.2:13.1:17.5 mixture of monomer Compound 8, isomer Compound 9, and fluorinated diol Compound 7 (2.9 grams total=4.1×10–3 mol of polymerizable monomer Compound 8) was degassed under vacuum and placed under a nitrogen atmosphere.

A sample vial was charged with 16.49 mg ($4.51\times10^{-5}$ mol) of ($\eta^3$-allyl) palladium chloride dimer, 31.12 milligrams ($0.91\times10^{-5}$ mol) of silver hexafluoroantimonate, and 1 mL of chlorobenzene. The catalyst mixture was stirred for 20 minutes at 20° C. The silver chloride formed was filtered off with a syringe filter (0.2 micrometer). The clear yellow catalyst solution was added to the degassed mixture of Compounds 8, 9, and 7 dissolved in 4 grams of chlorobenzene. After 5 hours the clear yellow solution had become hazy and a slight precipitate had formed. After 21.5 hours the stirring had stopped with a liquid top layer and a bottom solid layer. A small portion of the solution was analyzed by gc-fid. Based on gc-fid area counts, 32.7% of the original polymerizable monomer was still present indicating that conversion of the polymerizable monomer was 67.3%. The gel was dissolved by the addition of 0.7 grams of tetrahydrofuran and was precipitated by adding the resulting solution to 200 mL of hexanes. The filtered polymer was dried at 50° C. and 1 millibar to constant weight to give 1.13 grams of a white slightly fibrous solid. The final yield on this polymerization was 57.1% based on polymerizable monomer. The MW as determined by GPC relative to PS standards was $M_n$=31,000 and $M_w$=54,500.

Example 15

Polymerization of monomer Compound 11

This metal catalyzed polymerization was conducted in a nitrogen atmosphere. A 34:66 mixture of Compounds 11 and 12 (6.77 grams total=4.5×10$^{-3}$ mol polymerizable monomer Compound 11) was degassed under vacuum and placed under a nitrogen atmosphere.

A sample vial was charged with 16.49 mg ($4.5\times10^{-5}$ mol) of ($\eta^3$-allyl) palladium chloride dimer, 31.12 mg ($0.91\times10^{-5}$ mol) of silver hexafluoroantimonate, and 1.5 grams of chlorobenzene. The catalyst mixture was stirred for 20 minutes at 20° C. The silver chloride formed was filtered off with a syringe filter (0.2 micrometer). The clear yellow catalyst solution was added to the degassed mixture of Compounds 11 and 12 to give a clear amber solution. After 3 hours 2.25 grams of chlorobenzene were added to lower the viscosity of the clear amber solution which had become very viscous. A small portion of the solution was analyzed by gc-fid. The initial ratio of adducts were 1.87:1 and the final ratio was 36.6:1 indicating that conversion of the polymerizable monomer was 97.3%. After 23 hours 2.8 grams of ethyl acetate was added to lower viscosity further and then the polymer was precipitated by adding the solution to 200 mL of hexanes. The polymer was dried at 50° C. and 1 millibar to a constant weight to give 2.2 grams of a light gray powder/fibrous solid. The final yield on this polymerization was 96%. The MW as determined by GPC relative to PS standards was $M_n$=25,000 and $M_w$=476,000.

Example 16

Copolymerization of monomer Compound 2 with bicyclo[2.2.1]hept-5-ene-2-(1,1,1-trifluoro-2-trifluoromethylpropan-2-ol) (NBHFA)

This metal catalyzed polymerization was conducted in a nitrogen atmosphere. A 64.4:35.6 mixture of Compounds 2 and 3 (1.2 grams total=1.7×10$^{-3}$ mol of polymerizable monomer Compound 2) and NBHFA (0.12 grams=4×10$^{-4}$) mol was degassed under vacuum and placed under a nitrogen atmosphere.

A sample vial was charged with 7.78 mg ($2.1\times10^{-5}$ moles) of ($\eta^3$-allyl) palladium chloride dimer, 14.6 mg ($4.25\times10^{-5}$ moles) of silver hexafluoroantimonate, and 1.1 mL of chlorobenzene. The catalyst mixture was stirred for 20 minutes at 20° C. The silver chloride formed was filtered off with a syringe filter (0.2 micrometers). The clear yellow solution was added to the degassed mixture of monomer Compound 2, isomer Compound 3 (nortricyclane compound) and NBHFA. The solution remained clear for over 30 minutes. After 45 minutes the clear yellow solution had become hazy and a slight precipitate had formed. After 1 hour the stirring had stopped with a liquid top layer and a bottom solid layer. A small portion of the solution was analyzed by gc/fid. No monomer Compound 2 was found and only 5% of original Compound NBHFA remained indicating that both polymerizable monomers were incorporated into the copolymer at a monomer mole ratio of 80/20. Tetrahydrofuran 2.83 grams was added to the solution. The copolymer was precipitated from the tetrahydrofuran solution by adding it to 200 mL of hexanes. This precipitation process was repeated then dried at 50° C. and 1 millibar to a constant weight of 0.49 grams of a white powdery solid. The final yield of this polymerization was 55%.

The molecular weight (MW) (GPC relative to PS standards) was $M_n$ of 30,500 and $M_w$ of 50,000.

Example 17

Polymerization of Compounds 22 and 23 starting with a mixture of Compounds 22, 23, 24 and 25

This metal catalyzed polymerization was conducted in an inert atmosphere. A mixture containing 0.93 g polymerizable monomers (1.5×10$^{-3}$ mol) was dissolved in chlorobenzene and degassed under vacuum. This solution was placed under a nitrogen atmosphere. Compounds 24 and 25 were present in the mixture, but did not polymerize.

A sample vial was charged with 5.6 mg ($1.53\times10^{-5}$ mol) of ($\eta^3$-allyl) palladium chloride dimer (F.W.=365.9 g), 10.6 mg ($3.07\times10^{-5}$ mol) of silver hexafluoroantimonate (F.W.=343.6 g), and 0.7 g of chlorobenzene. The catalyst mixture was stirred for 20 min at 20° C. The silver chloride formed was filtered off with a syringe filter (0.2 μm) to give a clear yellow solution. The catalyst solution was added to the monomer solution described above. A clear yellow solution was obtained. In ≦18 h the clear yellow solution had separated into two phases, a liquid top phase and a bottom gel phase. A small portion of the solution was analyzed by GC after 48 h. The initial ratio of norbornene to nortricyclane adducts was 2.45:1 and the final ratio was 0.26:1 indicating that conversion of the polymerizable monomers was almost 89%. Upon addition of 2 g of tetrahydrofuran the gel dissolved to form a homogeneous solution. This solution was added to 200 mL of hexanes to precipitate the polymer. The polymer was filtered washed with hexanes and dried to give 0.72 g of a white powder. The final yield on this polymerization was 77.4%. The MW as determined by GPC relative to PS standards was $M_n$=38,500 and a $M_w$=78,200. By VUV-VASE the absorption coefficient at 157 nm on this polymer was determined to be 0.66 $\mu m^{-1}$. A base solubility test was conducted by placing drops of 0.26 N tetramethylammonium hydroxide (TMAH) onto a film. Films of this polymer were found to be base soluble.

Example 18

Polymerization of Compound 17 starting with a mixture of Compounds 17 and 18

This metal catalyzed polymerization was conducted in an inert atmosphere. A 0.97:1 mixture shown below along with some other minor components were dissolved in chlorobenzene (2.95 g) and degassed under vacuum to give a solution containing 1.78 g of polymerizable monomer ($4.1 \times 10^{-3}$ mol). This solution was placed under a nitrogen atmosphere.

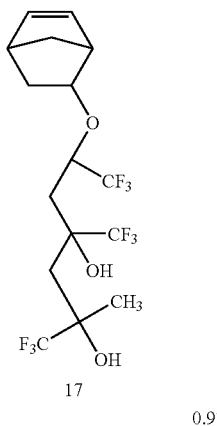
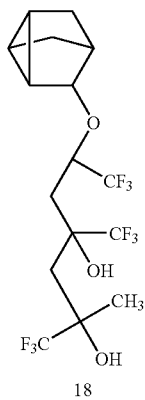

17          18
0.97:1

A sample vial was charged with 15.1 mg ($4.14 \times 10^{-5}$ mol) of ($\eta^3$-allyl) palladium chloride dimer, 28.6 mg ($8.3 \times 10^{-5}$ mol) of silver hexafluoroantimonate, and 1.9 g of chlorobenzene. The catalyst mixture was stirred for 20 min at 20° C. The silver chloride formed was filtered off with a syringe filter (0.2 μm) to give a clear yellow solution. The catalyst solution was added to the monomer solution containing 3.72 g of the monomer adducts containing 1.78 g ($4.1 \times 10^{-3}$ mol) of polymerizable monomer to give an amber/brownish hazy solution. After 48 h the solution was grayish/brown. A small portion of the solution was analyzed by GC. The initial ratio of adducts was 0.97:1 and the final ratio was 0.37:1 indicating that conversion of the polymerizable monomer was almost 61.8%. Upon addition of 2.25 g of tetrahydrofuran the solution became transparent but colored. The polymer was precipitated by adding the solution to 200 mL of hexanes. The polymer was filtered washed with hexanes and dried to give 1.0 g of a white powder. The final yield on this polymerization was 56.2%. The MW as determined by GPC relative to PS standards was $M_n$=11,200 and a $M_w$=22,000. Using a VUV-VASE the absorption coefficient at 157 nm on this polymer was determined to be 1.36 $\mu m^{-1}$. A base solubility test was conducted by placing drops of 0.26 N TMAH onto a film. Films of this polymer were found to be not soluble in base.

Example 19

Polymerization of Compound 27 starting with a mixture of Compound 27 and 28

A similar procedure using equivalent molar percentages as described above was used to prepare the homopolymer of Compound 27, except in this case, the polymerization was performed at 40° C. in order to fully dissolve the monomer in the reaction medium. The resulting polymer had a $M_n$=18,000; $M_w$=34,000.

Example 20

Polymerization of Compound 29

This monomer was polymerized at room temperature in a similar fashion to the procedures described above. The resulting polymer had a $M_n$=13,500; $M_w$=21,000.

Example 21

Preparation and polymerization of 6-bicyclo[2.2.1]hept-5-en-2-yloxy-2,6-bis(trifluoromethyl)-1,1,1,7,7,7-hexafluoroheptane-2ol (Compound 30)

The reaction product of propylene and HFA (2,6-bis(trifluoromethyl)-1,1,1,7,7,7-hexafluorohept-3-ene-2,6-diol) was obtained as described by Urry et al. and distilled at 65° C. and 4.5 torr. Into a 1 L ss autoclave was placed 39.0 g of this olefin, 4.6 g of 5% Pt on C (60% water wet), 4.6 g of 4% Rh on alumina, and 500 mL of isopropyl alcohol. The autoclave was purged with nitrogen then hydrogen and heated to 120° C. under 1100 psi hydrogen for 3.5 hours. The reactor was then cooled, vented, and discharged through an inline filter. The filtrate was concentrated in vacuo to give 35.1 g of a clear liquid, which was used without further purification. To 10.4 g of dichloroethane in a glass tube was added 10.2 g of the saturated diol and 2.5 g of quadricyclane. The tube was sealed and heated to 60° C. for 20 hours. The cooled contents of the glass vessel were concentrated in vacuo and then distilled at 62–64° C. and 0.2 torr to give 6.8 g of a clear colorless liquid which was a 97.7% pure (GC-FID) mixture of norbornene Compound 30 and nortricyclane isomer of Compound 30 in a 69:31 ratio.

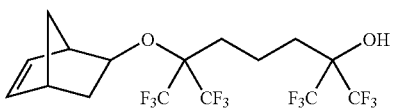

30

Monomer 30 was polymerized at room temperature under similar conditions to those described above, except that 170 mole % ethyl acetate based on polymerizable monomer was added to the reaction medium. The monomer conversion was determined by gas chromatography to be 58% after reacting one day. The polymer was precipitated by adding a tetrahydrofuran/chlorobenzene mixture of the reaction product to hexanes to form a grayish white solid. The polymer had a $M_n$=39,800 and a $M_w$=91,200 as determined by GPC relative to PS standards. Films of Poly (32) were spun from propylene glycol methyl ether acetate (PGMEA) onto several silicon wafers. These films were not soluble under normal base conditions, but it is understood by those skilled in the art that solubility can be achieved by copolymerization with a suitable comonomer of by derivatilization by a suitable acid labile group.

Example 22

Control of molecular weight

In some cases, it was found necessary to control the molecular weight of the polymer by adding a molecular weight modifier. We found ethyl acetate to be a particularly effective modifier. When the amount of ethyl acetate was too high (9 fold molar excess vs monomer), polymerization did ont occur. At the other extreme, addition of only 1–4 mol % ethyl acetate vs monomer led to high MW polymer. A summary of the effect of ethyl acetate on molecular weight of the homopolymer of Compound 2 is shown in FIG. 1.

Addition of ethyl acetate also led to a significant reduction in monomer conversion. Films cast from polymers of Compound 2 having a $M_n$ of <45,000 were soluble in 0.26 M TMAH.

Example 23

Transparency of polymer films

Propylene glycol methyl ether acetate (PGMEA) was used as the solvent for spinning polymer films. Solutions were filtered through a 0.2 micrometers filter prior to spinning.

The weight percent (wt %) solids was adjusted to give a viscosity that provided polymer thicknesses of approximately 100–200 nm. The wt % solids for each polymer is shown in Table 1. The solutions were dispensed onto an untreated silicon wafer, and then spun open bowl at 2000 rpm for 30 sec followed by a post apply bake (PAB) at 115° C. for 90 sec. The thickness of the films made from each polymer were measured and are listed in Table 1.

Spectra for the polymer films were measured using a VUV-VASE (vacuum ultraviolet variable angle spectroscopic ellipsometer). J.A. Woollam Co., Inc. provided the ellipsometry data and analysis between 146 nanometer and 1700 nanometer, at angles of incidence of 60° C. and 75° C. Conversion of the extinction coefficient to the base(10) absorption coefficient is accomplished by the transformation $$\alpha = \frac{4\pi k/\lambda}{\ln(10)},$$

where λ is the wavelength of light and k is the extinction coefficient. The absorption coefficient of the films from each polymer are listed in Table 1.

TABLE 1

Spectroscopic characterization of polymer films at 157 nm.

| monomer | α (μm$^{-1}$) | film thickness (nm) | wt % solids |
|---|---|---|---|
| 2 | 0.76 | 163 | 4.3 |
| 5 | 1.09 | 159 | 8 |
| 8 | 0.81 | 156 | 7.1 |

TABLE 1-continued

Spectroscopic characterization of polymer films at 157 nm.

| monomer | α (μm$^{-1}$) | film thickness (nm) | wt % solids |
|---|---|---|---|
| 11 | 1.02 | 156 | 5 |
| 14 | 1.36 | 178 | 8.1 |
| 17 | 1.36 | 192 | 8.8 |
| 22/23 | 0.66 | 223 | 8.7 |
| 27 | 0.71 | 159 | 8.7 |
| 29 | 0.59 | 154 | 8.7 |
| 30 | 0.90 | 252 | 8.0 |

Prior art homopolymers from norbornene monomers typically exhibit an absorption coefficient of greater than 1.5 μm$^{-1}$; therefore, co-monomers, which are often perfluoroolefins, are used instead of the homopolymers to meet the transparency requirement for 57nm lithography. The transparency requirement is usually an absorption coefficient less than 1.0 μm$^{-1}$. A bridged carbocyclic monomer of this invention provides adsorption coefficients less than 1.5 μm$^{-1}$ and less than 1.0 μm$^{-1}$ and can be used as homopolymers, or in copolymers, if desired, to provide even lower absorption coefficients The bridged carbocyclic compounds of this inventions homopolymers and when used in copolymers provide optical densities less than 1.5 μm$^{-1}$, and less than 1.0 μm$^{-1}$.

Example 24

Base Solubility

A polymer film made from Compound 5 was spun onto a silicon wafer as described for films made for measuring VUV spectra. A drop of standard 0.26N TMAH solution was placed on the wafer in three locations. After 30 seconds the wafer was rinsed with distilled water and dried. The three film regions exposed to base solution were found to dissolve. Those skilled in the art will recognize that placing a blocking group on the acidic OH would make this polymer useful in a positive photoresist formulation.

A copolymer film made from Compound 2 (80 mol %) and NBHFA (20 mol %) was spun onto a silicon wafer as described for films made for measuring optical spectra. A drop of standard 0.26N TMAH solution was placed on the wafer in three locations. After 30 seconds the wafer was rinsed with distilled water and dried. The three film regions exposed to base solution were found to dissolve. Those skilled in the art will recognize that placing a blocking group on the acidic OH would make this copolymer useful in a positive photoresist formulation.

While the invention has been described in detail and with reference to specific examples thereof, it will be apparent to one skilled in the art that various changes and modifications can be made therein without departing from the spirit and scope thereof.

Any and all patents and patent applications referred to herein are fully incorporated by reference.

We claim:

1. A bridged carbocyclic compound comprising a bridged carbocyclic ring, and an alkoxide group, wherein an oxygen of the alkoxide group is bonded to a ring-member of said bridged carbocyclic ring and to a carbon of the alkoxide group, and further wherein the carbon of the alkoxide group bonded to said oxygen has at least one fluorine-containing group bonded to said carbon and further wherein said alkoxide group has at least one hydroxyl group separated from said carbon that is bonded to said oxygen and said fluorine-containing group by at least one additional carbon that is bonded to said carbon that is bonded to said oxygen.

2. The bridged carbocyclic compound of claim 1, having the following structure:

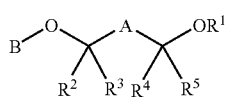
(I)

wherein A is a single bond, or a divalent organic group having 1 to 20 carbon atoms, and B is a bridged carbocyclic group of the type:

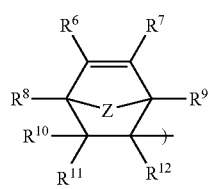
(II)

wherein Z is $CH_2$, $CHR^{13}$, $CR^{13}R^{14}$, $CH_2CH_2$, $CH_2CHR^{15}$, or a heteroatom; $R^1$ is a hydrogen, fluorinated alkylene alcohol group having 1 to 20 carbons, or a fluorinated cycloalkylene alcohol group having 1 to 20 carbons; and $R^{2-15}$ are each independently a hydrogen atom, a fluorine atom, an alkyl group, a fluorinated alkyl group, a cycloalkyl group, a fluorinated cycloalkyl group, a hydroxyl group, an alkoxyl group, a fluorinated alkoxyl group, an acyl group, an acyloxy group, a fluorinated acyl group, a fluorinated acyloxy group, or any of said groups having an amine group, or an ether group therein, and $R^3$ and $R^4$ may be bonded together to form a portion of a five or six member ring which may contain heteroatoms, with the proviso that at least one of $R^2$ and $R^3$ and at least one of $R^4$ and $R^5$ are independently a fluorine, a fluorinated alkyl group or a fluorinated cycloalkyl group.

3. The compound of claim 2, wherein $R^{2-15}$ are each independently a hydrogen atom, a fluorine atom, a hydroxyl group, or comprises 1 to 20 carbons and is an alkyl group, a fluorinated alkyl group, a cycloalkyl group, a fluorinated cycloalkyl group, an alkoxyl group, a fluorinated alkoxyl group, an acyl group, an acyloxy group, a fluorinated acyl group, a fluorinated acyloxy group, or any of said groups having an amine group, or an ether group therein.

4. The compound of claim 2, wherein $R^3$ and $R^4$ are independently a fluorine atom, a fluorinated alkyl group or a fluorinated cycloalkyl group.

5. The compound of claim 2, wherein A is a single bond or comprises 1 to 15 carbons and is an alkylene group, a hydroxyl substituted alkylene group, a fluorinated alkylene group, a hydroxyl substituted fluorinated alkylene group, a cycloalkylene group, a hydroxyl substituted cycloalkylene group, a fluorinated cycloalkylene group, or a hydroxyl substituted fluorinated cycloalkylene group.

6. The compound of claim 2 wherein A is a single bond, or comprises 1 to 10 carbons and is an alkylene group, a hydroxyl substituted alkylene group, a fluorinated alkylene group, a hydroxyl substituted fluorinated alkylene group, a cycloalkylene group, a hydroxyl substituted cycloalkylene group, a fluorinated cycloalkylene group, or a hydroxyl substituted fluorinated cycloalkylene group.

7. The compound of claim 2 wherein A is selected from the group consisting of methylene; ethane-1,1-diyl (ethylidene); ethane-1,2-diyl (ethylene); propane -1,1-diyl; propane-1,2-diyl; propane-1,3-diyl; butane-1,1-diyl; butane-1,2-diyl; butane-1,3-diyl; butane-1,4-diyl; butane-2,3-diyl; pentane-1,1-diyl; pentane-1,2-diyl; pentane-1,3-diyl; pentane-1,4-diyl; pentane-1,5-diyl; hexane-1,6-diyl; 2-methylpropane-1,2-diyl; 2-methylpropane-1,3diyl; 3-methylbutane-1,3-diyl; 2-methylbutane-1,3-diyl; 2-methylbutane-1,4-diyl; 2,3-dimethylbutane,-2,3-diyl; 2,5-dimethylhexane-1,6-diyl; 3-oxapentane-1,5-diyl; cyclopropane-1,1-diyl; cyclopropane-1,2-diyl; cyclobutane-1,1-diyl; cyclobutane-1,2-diyl; cyclobutane-1,3-diyl; cyclopentane-1,1-diyl; cyclopentane-1,2-diyl; cylopentane-1,3-diyl; cyclohexane-1,1-diyl; cyclohexane-1,2-diyl; cyclohexane-1,3-diyl; cyclohexane-1,4-diyl; methylcyclohexane-1,4-diyl; 1,1,2,2-tetrafluoroethane-1,2-diyl; 3,3,3-trifluoropropane-1,2-diyl; and 2-hydroxypropane-1,3-diyl;

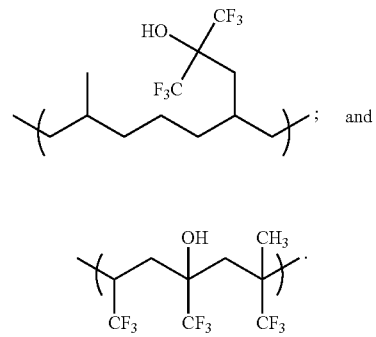

8. The compound of claim 2, wherein Z is selected from the group consisting of oxygen, a nitrogen group, sulfur, and $CH_2$.

9. The compound of claim 2, wherein Z is $CH_2$.

10. The compound of claim 2 wherein $R^{2-15}$ are each independently a hydrogen atom, a fluorine atom, a hydroxyl group, or comprises 1 to 20 carbons and is an alkyl group, a fluorinated alkyl group, a cycloalkyl group, a fluorinated cycloalkyl group, an alkoxyl group, or a fluorinated alkoxyl group.

11. The compound of claim 2 wherein $R^{6-12}$ are each independently a fluorinated alkyl having 1 to 10 carbons, a fluorinated alkoxy group having 1 to 10 carbons, a hydrogen atom or a fluorine atom.

12. The compound of claim 2 wherein $R^1$ is a hydrogen, $R^4$ and $R^5$ are each independently a fluorinated alkyl group having 1 to 5 carbons, a fluorinated cyclic alkyl group having 1 to 5 carbons or a fluorine atom.

13. The compound of claim 2 wherein $R^1$ is a hydrogen, and $R^2$, $R^3$, R4 and $R^5$ are —$CF_3$.

14. The compound of claim 2 wherein B is norbornenyl, or 7-oxanorbornenyl.

15. The compound of claim 2 wherein said compound comprises seven or more fluorine atoms.

16. The compound of claim 2 comprising the following structure:

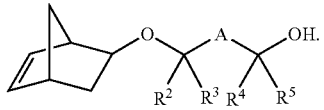

(IV)

17. The compound of claim 16, wherein A is a single bond or any linear or branched alkyl group having 1 to 6 carbons, or fluorinated alkyl group having 1 to 15 carbons, or cycloalkyl group having 4 to 6 carbons, or fluorinated cycloalkyl group having 4 to 6 carbons, and wherein $R^2$ is a hydrogen atom, a fluorine atom, an alkyl group having 1 to 6 carbons, a fluorinated alkyl group having 1 to 6 carbons, a cycloalkyl group having 4 to 6 carbons, or a fluorinated cyclo alkyl group having 4 to 6 carbons, and $R^{3-5}$ are each independently a fluorinated alkyl group having 1 to 3 carbons or a fluorinated cycloalkyl group having 1 to 3 carbons.

18. The compound of claim 16, selected from the group consisting of:

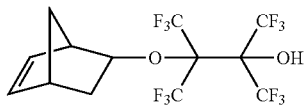

3-bicyclo[2.2.1]hept-5-en-2-yloxy-2,3-bis(trifluoromethyl)-1,1,1,4,4,4-hexafluorobutan-2-ol

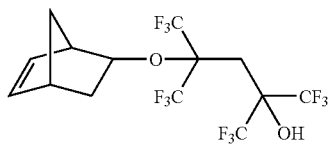

4-bicyclo[2.2.1]hept-5-en-2-yloxy-2,4-bis(trifluoromethyl)-1,1,1,5,5,5-hexafluoropentan-2-ol

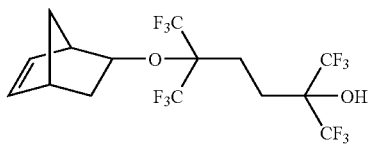

5-bicyclo[2.2.1]hept-5-en-2-yloxy-2,5-bis(trifluoromethyl)-1,1,1,6,6,6-hexafluorohexan-2-ol

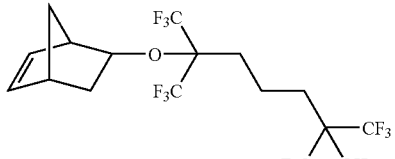

6-bicyclo[2.2.1]hept-5-en-2-yloxy-2,6-bis(trifluoromethyl)-1,1,1,7,7,7-hexafluoroheptan-2-ol -continued

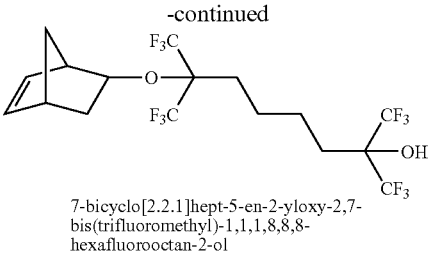

7-bicyclo[2.2.1]hept-5-en-2-yloxy-2,7-bis(trifluoromethyl)-1,1,1,8,8,8-hexafluorooctan-2-ol

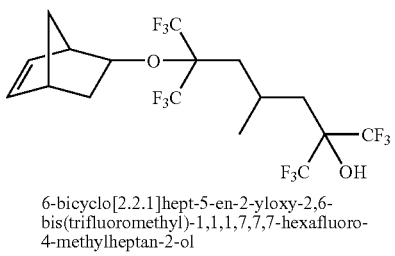

6-bicyclo[2.2.1]hept-5-en-2-yloxy-2,6-bis(trifluoromethyl)-1,1,1,7,7,7-hexafluoro-4-methylheptan-2-ol

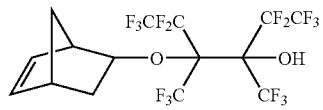

4-bicyclo[2.2.1]hept-5-en-2-yloxy-3,4-bis(trifluoromethyl)-1,1,1,2,2,5,5,6,6,6-decafluorohexan-3-ol

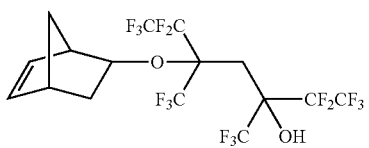

5-bicyclo[2.2.1]hept-5-en-2-yloxy-3,5-bis(trifluoromethyl)-1,1,1,2,2,6,6,7,7,7,-decafluoroheptan-3-ol

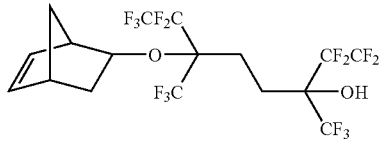

6-bicyclo[2.2.1]hept-5-en-2-yloxy-3,6-bis(trifluoromethyl)-1,,1,2,2,7,7,8,8,8-nonafluorooctan-3-ol

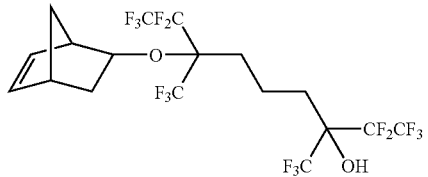

7-bicyclo[2.2.1]hept-5-en-2-yloxy-3,7-bis(trifluoromethyl)-1,1,1,2,2,8,8,9,9,9-decafluorononan-3-ol

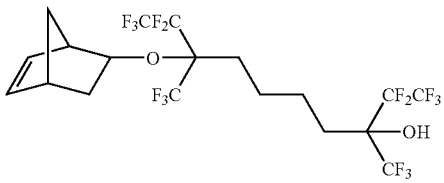

8-bicyclo[2.2.1]hept-5-en-2-yloxy-3,8-bis(trifluoromethyl)-1,1,1,2,2,9,9,10,10,10-decafluorodecan-3-ol

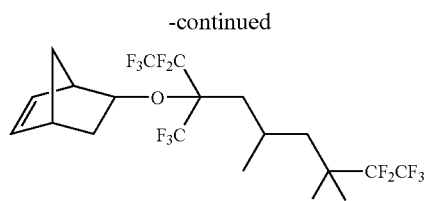

7-bicyclo[2.2.1]hept-5-en-2-yloxy-3,7-
bis(trifluoromethyl)-1,1,1,2,2,8,8,9,9,9-
decafluoro-5-methylnonan-3-ol

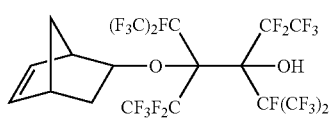

4-bicyclo[2.2.1]hept-5-en-2-yloxy-3,4-
bis[1,2,2,2-tetrafluoro-1-
(trifluoromethyl)ethyl]-1,1,1,2,2,5,5,6,6,6-
decafluorohexan-3-ol

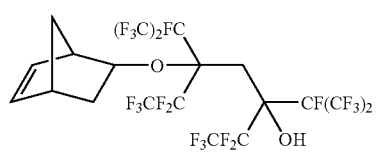

5-bicyclo[2.2.1]hept-5-en-2-yloxy-3,5-
bis[1,2,2,2-tetrafluoro-1-
(trifluoromethyl)ethyl]-1,1,1,2,2,6,6,7,7,7-
decafluoroheptan-3-ol

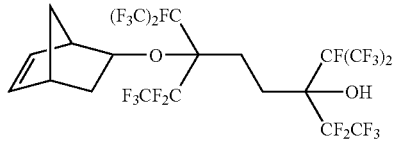

6-bicyclo[2.2.1]hept-5-en-2-yloxy-3,6-
bis[1,2,2,2-tetrafluoro-1-
(trifluoromethyl)ethyl]-1,1,1,2,2,7,7,8,8,8-
decafluorooctan-3-ol

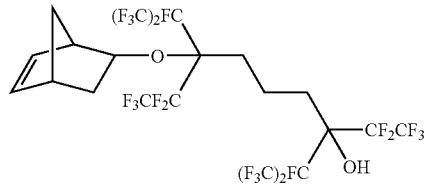

7-bicyclo[2.2.1]hept-5-en-2-yloxy-3,7-
bis[1,2,2,2-tetrafluoro-1-
(trifluoromethyl)ethyl]-1,1,1,2,2,8,8,9,9,9-
decafluorononan-3-ol

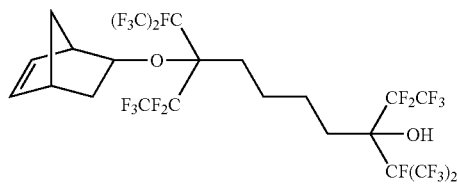

8-bicyclo[2.2.1]hept-5-en-2-yloxy-3,8-
bis[1,2,2,2-tetrafluoro-1-
(trifluoromethyl)ethyl]-1,1,1,2,2,9,9,10,10,10-
decafluorodecan-3-ol

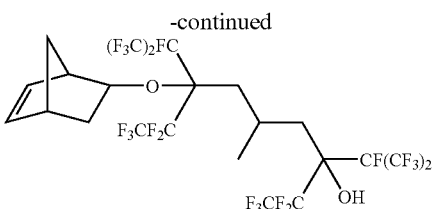

7-bicyclo[2.2.1]hept-5-en-2-yloxy-3,7-
bis[1,2,2,2-tetrafluoro-1-
(trifluoromethyl)ethyl]-1,1,1,2,2,8,8,9,9,9-
decafluoro-5-methylnonan-3-ol

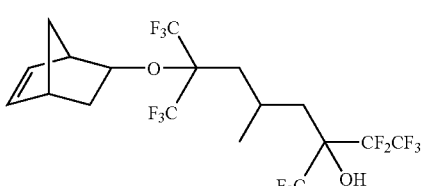

7-bicyclo[2.2.1]hept-5-en-2-yloxy-3,7-
bis(trifluoromethyl)-1,1,1,2,2,8,8,8-
octafluoro-5-methyloctan-3-ol

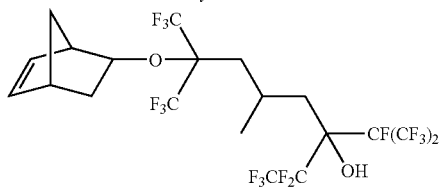

7-bicyclo[2.2.1]hept-5-en-2-yloxy-
1,1,1,2,2,8,8,8-octafluoro-5-methyl-3-
[1,2,2,2-tetrafluoro-1-
(trifluoromethyl)ethyl]-7-
(trifluoromethyl)octan-3-ol

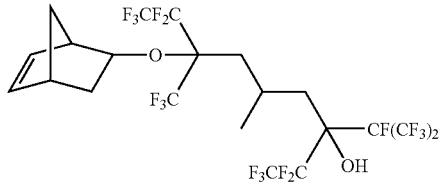

7-bicyclo[2.2.1]hept-5-en-2-yloxy-
1,1,1,2,2,8,8,9,9,9-decafluoro-5-methyl-3-
[1,2,2,2-tetrafluoro-1-
(trifluoromethyl)ethyl]-7-
(trifluoromethyl)nonan-3-ol

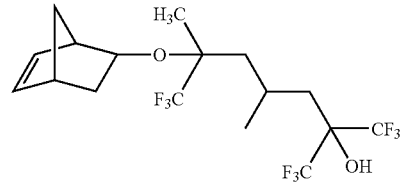

6-bicyclo[2.2.1]hept-5-en-2-yloxy-
1,1,1,7,7,7-hexafluoro-4,6-dimethyl-2-
(trifluoromethyl)heptan-2-ol

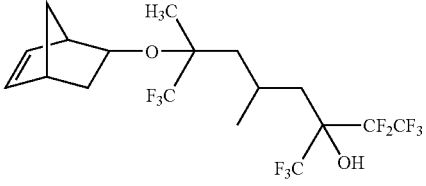

7-bicyclo[2.2.1]hept-5-en-2-yloxy-
1,1,1,2,2,8,8,8-octafluoro-5,7-dimethyl-3-
(trifluoromethyl)octan-3-ol

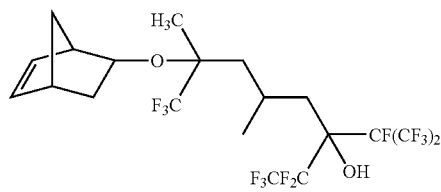

7-bicyclo[2.2.1]hept-5-en-2-yloxy-
1,1,1,2,2,8,8,8-octafluoro-5,7-dimethyl-3-
[1,2,2,2-tetrafluoro-1-
(trifluoromethyl)ethyl]octan-3-ol

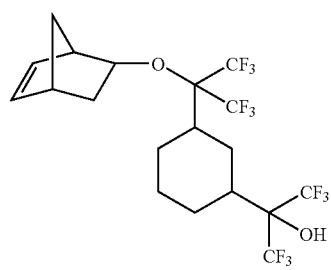

2-{3-[1-bicyclo[2.2.1]hept-5-en-2-yloxy-
2,2,2-trifluoro-1-
(trifluoromethyl)ethyl]cyclohexyl}-
1,1,1,3,3,3-hexafluoropropan-2-ol

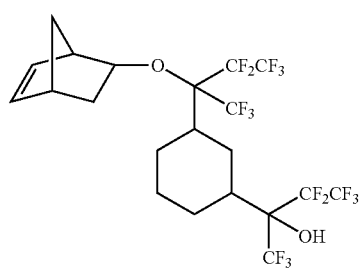

2-{3-[1-bicyclo[2.2.1]hept-5-en-2-yloxy-
2,2,3,3,3-pentafluoro-1-
(trifluoromethyl)propyl]cyclohexyl}-
1,1,1,3,3,4,4,4-octafluorobutan-2-ol

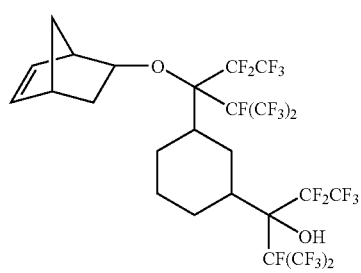

3-{3-[1-bicyclo[2.2.1]hept-5-en-2-yloxy-
2,2,3,3,3-pentafluoro-1-[1,2,2,2-
tetrafluoro-1-
(trifluoromethyl)ethyl]propyl}cyclohexyl}-
1,1,1,2,4,4,5,5,5-nonafluoro-2-
(trifluoromethyl)pentan-3-ol

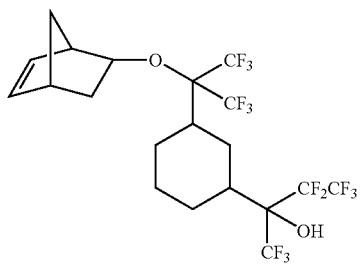

2-{3-[1-bicyclo[2.2.1]hept-5-en-2-yloxy-
2,2,2-trifluoro-1-
(trifluoromethyl)ethyl]cyclohexyl}-
1,1,1,3,3,4,4,4-octafluorobutan-2-ol

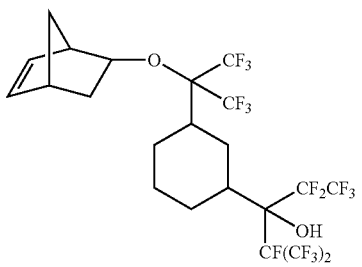

3-{3-[1-Bicyclo[2.2.1]hept-5-en-2-yloxy-
2,2,2-trifluoro-1-trifluoromethyl-ethyl]-
cyclohexyl}-1,1,1,2,2,4,5,5,5-nonafluoro-
4-trifluoromethyl-pentan-3-ol

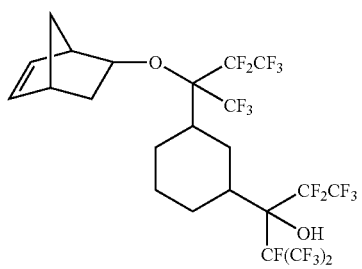

3-{3-[1-Bicyclo[2.2.1]hept-5-en-2-yloxy-
2,2,3,3,3-pentafluoro-1-trifluoromethyl-
propyl]-cyclohexyl}-1,1,1,2,2,4,5,5,5-
nonafluoro-4-trifluoromethyl-pentan-3-ol

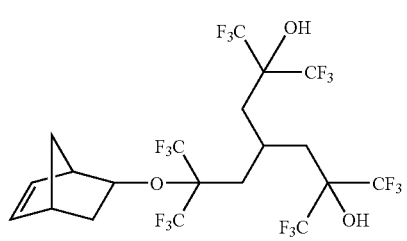

4-[bicyclo[2.2.1]hept-5-en-2-yloxy-
3,3,3-trifluoro-2-(trifluoromethyl)-
propyl]-2,6-bis(trifluoromethyl)-
1,1,1,7,7,7-hexafluoroheptane-2,6-diol -continued

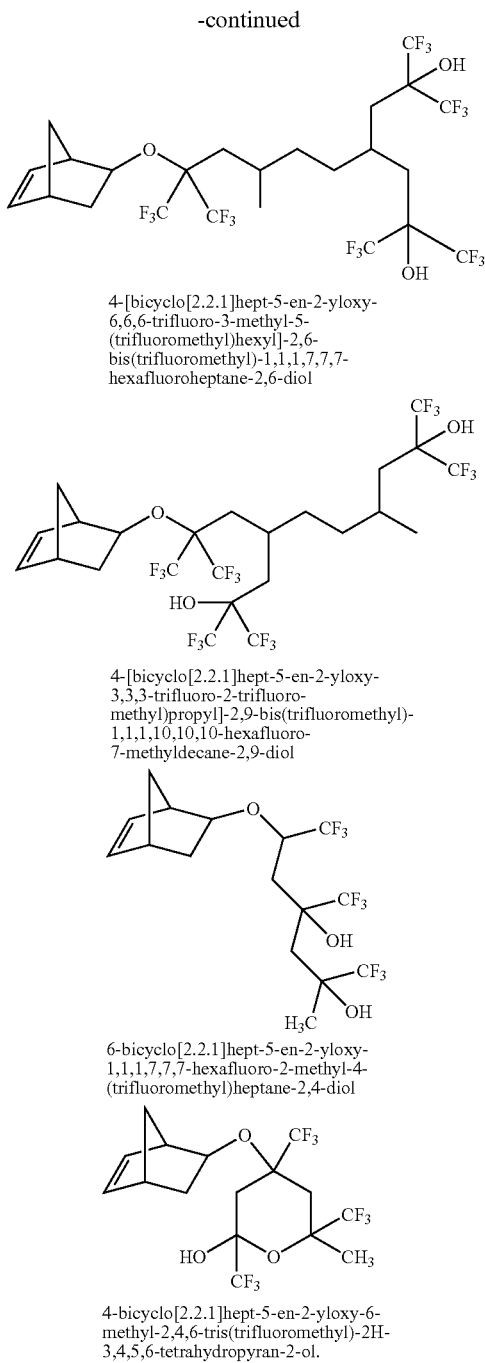

4-[bicyclo[2.2.1]hept-5-en-2-yloxy-
6,6,6-trifluoro-3-methyl-5-
(trifluoromethyl)hexyl]-2,6-
bis(trifluoromethyl)-1,1,1,7,7,7-
hexafluoroheptane-2,6-diol 4-[bicyclo[2.2.1]hept-5-en-2-yloxy-
3,3,3-trifluoro-2-trifluoro-
methyl)propyl]-2,9-bis(trifluoromethyl)-
1,1,1,10,10,10-hexafluoro-
7-methyldecane-2,9-diol 6-bicyclo[2.2.1]hept-5-en-2-yloxy-
1,1,1,7,7,7-hexafluoro-2-methyl-4-
(trifluoromethyl)heptane-2,4-diol 4-bicyclo[2.2.1]hept-5-en-2-yloxy-6-
methyl-2,4,6-tris(trifluoromethyl)-2H-
3,4,5,6-tetrahydropyran-2-ol.

19. The bridged carbocyclic compound of claim 1 comprising the following structure:

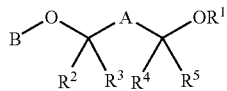

(I)

wherein A is a single bond, or a divalent organic group having 1 to 20 carbon atoms, and B is a bridged carbocyclic group of the type:

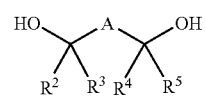

(III)

wherein Z is $CR_2$, $CHR^{13}$, $CR^{13}R^{14}$, $CH_2CH_2$, $CH_2CHR^{15}$ or a heteroatom; $R^1$ is a hydrogen, fluorinated alkylene alcohol group, or a fluorinated cycloalkylene alcohol group having 1 to 20 carbons; and $R^{2-10,12-15}$ are each independently a hydrogen atom, a fluorine atom, an alkyl group, a fluorinated alkyl group, a cycloalkyl group, a fluorinated cycloalkyl group, a hydroxyl group, an alkoxyl group, a fluorinated alkoxyl group, an acyl group, an acyloxy group, a fluorinated acyl group, a fluorinated acyloxy group, or any of the said groups having an amine group, an ether group therein, and $R^3$ and $R^4$ may be bonded together to form a portion of a five or six member ring which may contain heteroatoms, with the proviso that at least one of $R^2$ and $R^3$ and at least one of $R^4$ and $R^5$ are independently a fluorine, a fluorinated alkyl group or a fluorinated cycloalkyl group.

20. The carbocyclic compound of claim 1 obtained from by a method comprising the steps of:
combining a bridged carboxylic reaction material and a fluorinated alcohol to form a reaction mixture and
reacting said bridged carboxylic reaction material and said fluorinated alcohol to produce said bridged carbocyclic compound.

21. The carbocyclic compound of claim 20 wherein said carboxylic reaction material is selected from the group consisting of quadricyclane, tetracyclo[4.2.0.0$^{2,8}$.0$^{5,7}$] octane, thioquadricyclane, oxaquadricyclane, or substituted derivative of quadricyclane, tetracyclo[4.2.0.0$^{2,8}$.0$^{5,7}$ ] octane, thioquadricyclane, or oxaquadricyclane.

22. The carbocyclic compound of claim 20 wherein said fluorinated alcohol and said bridged carbocyclic reaction material are combined in a molar ratio between from 1:1 to3:1.

23. The carbocyclic compound of claim 20 wherein said reaction mixture further comprises a solvent selected from the group consisting of an ether solvent, an aromatic solvent a nitrile, or an alkyl alcohol, or mixtures of said solvents.

24. The carbocyclic compound of claim 20 wherein said reaction mixture further comprises an acid or an acid catalyst.

25. The carbocyclic compound of claim 20 further wherein said reacting step produces an isomer of said bridged carbocyclic compound.

26. The carbocyclic compound of claim 20 wherein the fluorinated alcohols have the following structural formula:

wherein A is a single bond, or a divalent organic group having 1 to 20 carbon atoms, $R^2$, $R^3$, $R^4$, and $R^5$ are each independently a hydrogen atom, a fluorine atom, an alkyl group, a fluorinated alkyl group, a cycloalkyl group, a fluorinated cycloalkyl group, a hydroxyl group, an alkoxyl group, a fluorinated alkoxyl group, an acyl group, an acyloxy group, a fluorinated acyl group, a fluorinated acyloxy group, or any of said groups having an amine group, or an ether group therein, and $R^3$ and $R^4$ may be bonded together to form a portion of a five or six member ring which may contain heteroatoms, with the proviso that at least one of $R^2$ and $R^3$ and at least one of $R^4$ and $R^5$ is fluorine, a fluorinated alkyl group or a fluorinated cycloalkyl group.

27. The carbocyclic compound of claim 20 wherein said fluorinated alcohols are selected from the group consisting of:

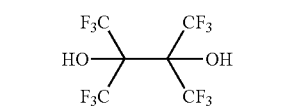

2,3-bis(trifluoromethyl)-1,1,1,4,4,4-hexafluorobutane-2,3-diol

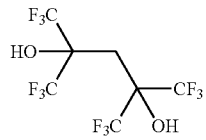

2,4-bis(trifluoromethyl)-1,1,1,5,5,5-hexafluoropentane-2,4-diol

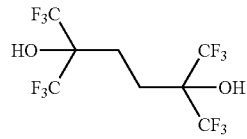

2,5-bis(trifluoromethyl)-1,1,1,6,6,6-hexafluorohexane-2,5-diol

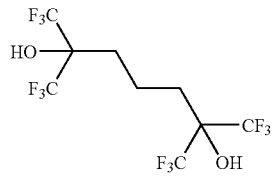

2,6-bis(trifluoromethyl)-1,1,1,7,7,7-hexafluoroheptane-2,6-diol

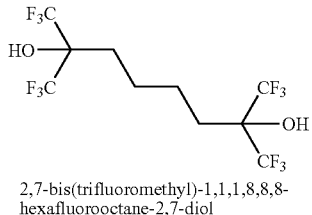

2,7-bis(trifluoromethyl)-1,1,1,8,8,8-hexafluorooctane-2,7-diol

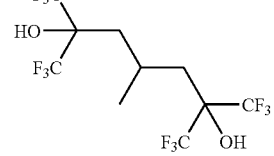

2,6-bis(trifluoromethyl)-1,1,1,7,7,7-hexafluoro-4-methylheptane-2,6-diol

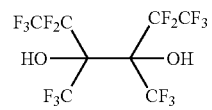

3,4-bis(trifluoromethyl)-1,1,1,2,2,5,5,6,6,6-decafluorohexane-3,4-diol

-continued

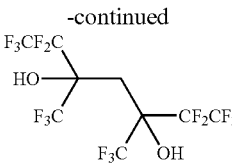

3,5-bis(trifluoromethyl)-1,1,1,2,2,6,6,7,7,7-decafluoroheptane-3,5-diol

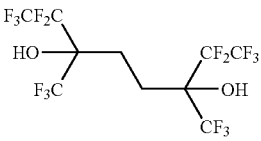

3,6-bis(trifluoromethyl)-1,1,1,2,2,7,7,8,8-nonafluorooctane-3,6-diol

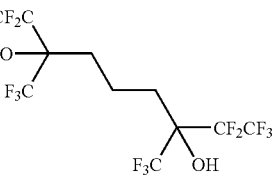

3,7-bis(trifluoromethyl)-1,1,1,2,2,8,8,9,9,9-decafluorononane-3,7-diol

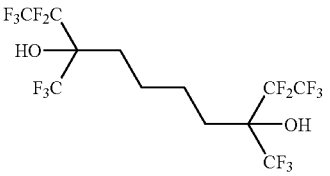

3,8-bis(trifluoromethyl)-1,1,1,2,2,9,9,10,10,10-decafluorodecane-3,8-diol

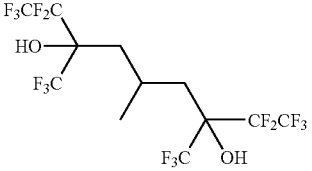

3,7-bis(trifluoromethyl)-1,1,1,2,2,8,8,9,9,9-decafluoro-5-methylnonane-3,7-diol

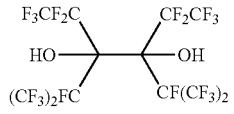

3,4-bis[1,2,2,2-tetrafluoro-1-(trifluoromethyl)ethyl]-1,1,1,2,2,5,5,6,6,6-decafluorohexane-3,4-diol

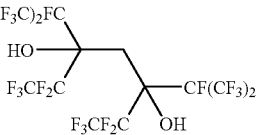

3,5-bis[1,2,2,2-tetrafluoro-1-(trifluoromethyl)ethyl]-1,1,1,2,2,6,6,7,7,7-decafluoroheptane-3,5-diol

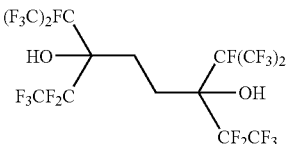

3,6-bis[1,2,2,2-tetrafluoro-1-(trifluoromethyl)ethyl]-1,1,1,2,2,7,7,8,8,8-decafluorooctane-3,6-diol

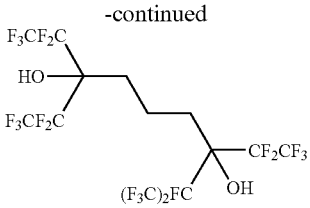

3,7-bis[1,2,2,2-tetrafluoro-1-
(trifluoromethyl)ethyl]-1,1,1,2,2,8,8,9,9,9-
decafluorononane-3,7-diol

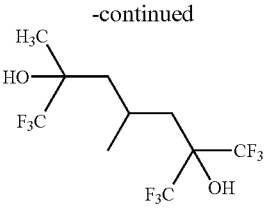

3,8-bis[1,2,2,2-tetrafluoro-1-
(trifluoromethyl)ethyl]-
1,1,1,2,2,9,9,10,10,10-decafluorodecane-3,8-diol

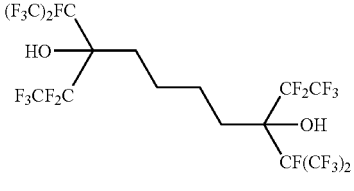

3,7-bis[1,2,2,2-tetrafluoro-1-
(trifluoromethyl)ethyl]-1,1,1,2,2,8,8,9,9,9-
decafluoro-5-methylnonane-3,7-diol

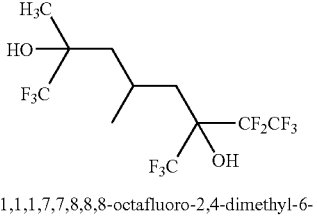

2,6-bis(trifluoromethyl)-1,1,1,7,7,8,8,8-
octafluoro-4-methyloctane-2,6-diol

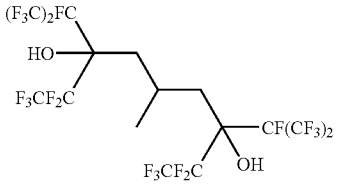

1,1,1,7,7,8,8,8,-octafluoro-4-methyl-6-
[1,2,2,2-tetrafluoro-1-(trifluoromethyl)ethyl]-
2-(trifluoromethyl)octane-2,6-diol

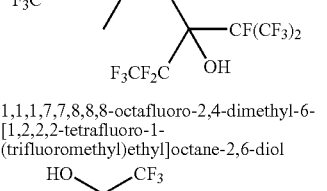

1,1,1,2,2,8,8,9,9,9-decafluoro-5-methyl-3-
[1,2,2,2-tetrafluoro-1-(trifluoromethyl)ethyl]-
7-(trifluoromethyl)nonane-3,7-diol

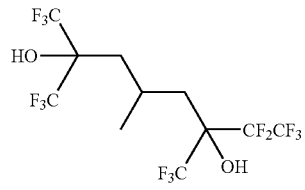

1,1,1,7,7,7-hexafluoro-2,4-dimethyl-6-
(trifluoromethyl)heptane-2,6-diol

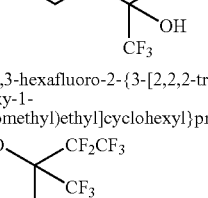

1,1,1,7,7,8,8,8-octafluoro-2,4-dimethyl-6-
(trifluoromethyl)octane-2,6-diol

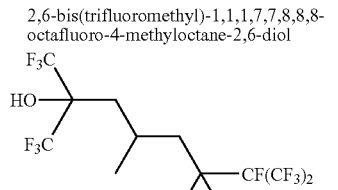

1,1,1,7,7,8,8,8-octafluoro-2,4-dimethyl-6-
[1,2,2,2-tetrafluoro-1-
(trifluoromethyl)ethyl]octane-2,6-diol

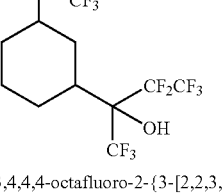

1,1,1,3,3,3-hexafluoro-2-{3-[2,2,2-trifluoro-
1-hydroxy-1-
(trifluoromethyl)ethyl]cyclohexyl}propan-2-ol

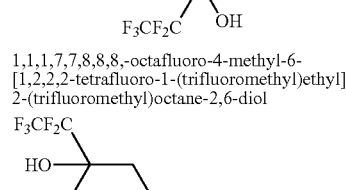

1,1,1,3,3,4,4,4-octafluoro-2-{3-[2,2,3,3,3-
pentafluoro-1-hydroxy-1-
(trifluoromethyl)propyl]cyclohexyl}butan-2-ol

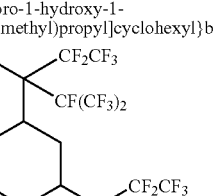

1,1,1,2,4,4,5,5,5-nonafluoro-3-(3-
{2,2,3,3,3-pentafluoro-1-hydroxy-1-
[1,2,2,2-tetrafluoro-
(trifluoromethyl)ethyl]propyl}cyclohexyl)-2-
(trifluoromethyl)pentan-3-ol -continued

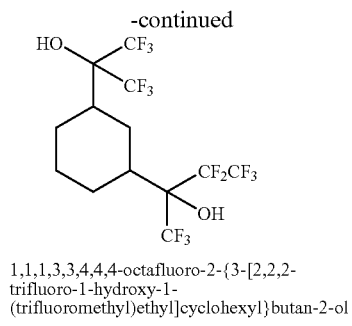

1,1,1,3,3,4,4,4-octafluoro-2-{3-[2,2,2-trifluoro-1-hydroxy-1-(trifluoromethyl)ethyl]cyclohexyl}butan-2-ol

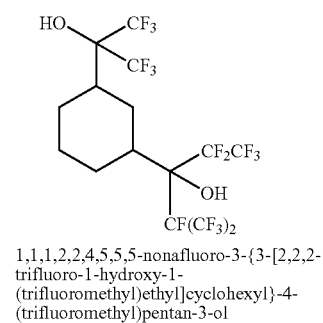

1,1,1,2,2,4,5,5,5-nonafluoro-3-{3-[2,2,2-trifluoro-1-hydroxy-1-(trifluoromethyl)ethyl]cyclohexyl}-4-(trifluoromethyl)pentan-3-ol

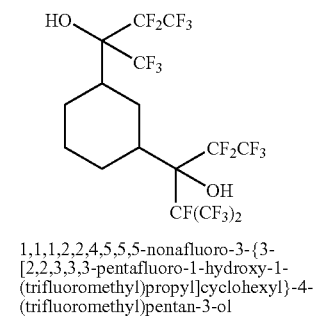

1,1,1,2,2,4,5,5,5-nonafluoro-3-{3-[2,2,3,3,3-pentafluoro-1-hydroxy-1-(trifluoromethyl)propyl]cyclohexyl}-4-(trifluoromethyl)pentan-3-ol

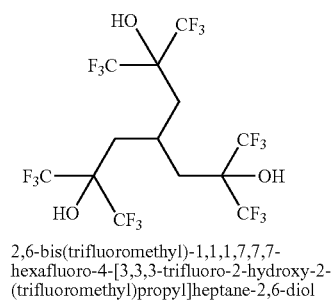

2,6-bis(trifluoromethyl)-1,1,1,7,7,7-hexafluoro-4-[3,3,3-trifluoro-2-hydroxy-2-(trifluoromethyl)propyl]heptane-2,6-diol

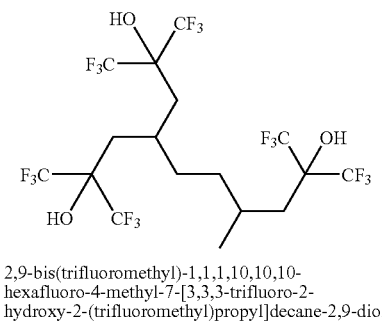

2,9-bis(trifluoromethyl)-1,1,1,10,10,10-hexafluoro-4-methyl-7-[3,3,3-trifluoro-2-hydroxy-2-(trifluoromethyl)propyl]decane-2,9-diol -continued

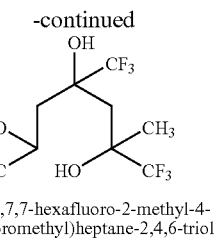

1,1,1,7,7,7-hexafluoro-2-methyl-4-(trifluoromethyl)heptane-2,4,6-triol

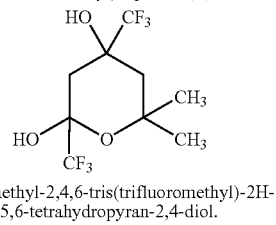

6-methyl-2,4,6-tris(trifluoromethyl)-2H-3,4,5,6-tetrahydropyran-2,4-diol.

28. The carbocyclic compound of claim 20 wherein after said reacting step, the method further comprises the step of polymerizing said bridged carbocyclic compound.

29. A method of polymerizing a bridged carbocyclic compound to form a polymer comprising the step of combining a metal catalyst, a molecular weight modifier and a bridged carbocyclic compound, wherein said bridged carbocyclic compound comprises a bridged carbocyclic ring, and an alkoxide group, wherein an oxygen of the alkoxide group is bonded to a ring-member of said bridged carbocyclic ring and to a carbon of the alkoxide group, and further wherein the carbon of the alkoxide group bonded to said oxygen has at least one fluorine-containing group bonded to said carbon and further wherein the alkoxide group has at least one hydroxyl group separated from said carbon that is bonded to said oxygen and said fluorine-containing group by at least one additional carbon that is bonded to said carbon that is bonded to said oxygen.

30. The method of claim 29 wherein said molecular weight modifier is ethyl acetate.

31. A polymer comprising polymerized units of a bridged carbocyclic compound comprising a bridged carbocyclic ring, and an alkoxide group, wherein an oxygen of the alkoxide group is bonded to a ring-member of said bridged carbocyclic ring and to a carbon of the alkoxide group, and further wherein the carbon of the alkoxide group bonded to said oxygen has at least one fluorine-containing group bonded to said carbon and wherein the alkoxide group has at least one hydroxyl group separated from said carbon that is bonded to said oxygen and said fluorine-containing group by at least one additional carbon that is bonded to said carbon that is bonded to said oxygen.

32. The polymer of claim 31 wherein said polymerized units comprise the following formula:

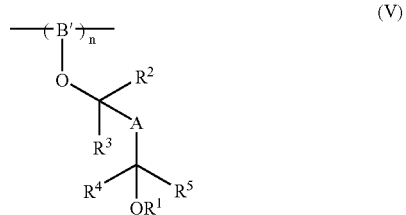

(V)

wherein A is a single band, or a divalent organic group having 1 to 20 carbon atoms, and B' is a bridged carbocyclic group of the type:

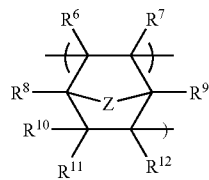

(VI)

wherein Z is CH$_2$, CHR$^{13}$, CR$^{13}$R$^{14}$, CH$_2$CH$_2$, $_{CH2}$CHR$^{15}$, or a heteroatom; R$^1$ is a hydrogen, fluorinated alkylene alcohol group, or a fluorinated cycloalkylene alcohol group having 1 to 20 carbons; and R$^{2-15}$ are each independently a hydrogen atom, a fluorine atom, an alkyl group, a fluorinated alkyl group, a cycloalkyl group, a fluorinated cycloalkyl group, a hydroxyl group, an alkoxyl group, a fluorinated alkoxyl group, an acyl group, an acyloxy group, a fluorinated acyl group, a fluorinated acyloxy group, or any of said groups having an amine group, or an ether group therein, and R$^3$ and R$^4$ may be bonded together to form a portion of a five or six member ring which may contain heteroatoms, with the proviso that at least one of R$^2$ and R$^3$ and at least one of R$^4$ and R$^5$ are independently a fluorine, a fluorinated alkyl group or a fluorinated cycloalkyl group, and n is 3 to 500.

33. The polymer of claim 31 further comprising polymerized units of at least one other ethylenically unsaturated monomer.

34. The polymer of claim 33 wherein said ethylenically unsaturated monomers are selected from the group consisting of C$_1$–C$_{18}$ alkyl (meth)acrylate monomers, vinyl aromatic monomers, vinyl esters, vinyl-unsaturated carboxylic acids monomers, nitrogen-containing vinyl unsaturated monomers, dienes, ethylene, norbornene, hydroxyethyl (meth)acrylate, hydroxypropyl(meth)acrylate, fluorinated olefins, partially and fully fluorinated derivatives of propylene, butylene, and isobutylene, fluorinated derivatives of maleic anhydride, fluoro-(meth)acrylates (vinyl substituted), and fluoro-methacrylates (methyl substituted), and fluorovinyl ethers.

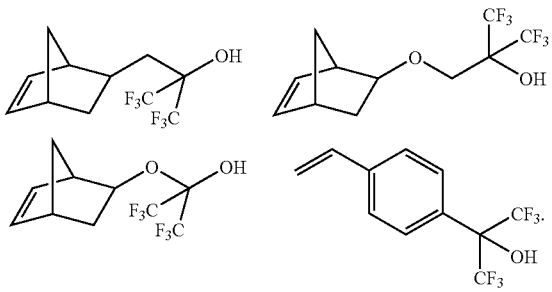

35. The polymer of claim 33 wherein said ethylenically unsaturated monomer comprises acid-labile groups selected from the group consisting of tertiary alkoxy groups, tert-alkoxycarbonyl groups, alkoxy methyl groups, cyclic derivatives of alkoxy methyl groups.

36. The polymer of claim 33 used in a photoresist composition.

37. A method of creating a patterned image on a substrate to form a circuit component comprising:
applying a photoresist composition comprising the polymer of claim 31 to a substrate and exposing said photoresist composition to energy to produce a patterned image on said substrate.

* * * * *

UNITED STATES PATENT AND TRADEMARK OFFICE
CERTIFICATE OF CORRECTION

PATENT NO. : 7,138,550 B2 Page 1 of 1
APPLICATION NO. : 10/784377
DATED : November 21, 2006
INVENTOR(S) : Richard Van Court Carr et al.

It is certified that error appears in the above-identified patent and that said Letters Patent is hereby corrected as shown below:

Column 48, Line 63

In Claim 13, the 4 after R should be superscript. Should read and $R^2$, $R^3$, $R^4$ and $R^5$ are...........

Column 56, Line 12

In Claim 19, should read........wherein Z is $CH_2$, $CHR^{13}$.......

Column 63, Line 15

In Claim 32, should read.....wherein Z is $CH_2$, $CHR^{13}$, $CR^{13}R^{14}$, $CH_2,CH_2CHR^{15}$.....

Signed and Sealed this

Sixth Day of March, 2007

JON W. DUDAS
*Director of the United States Patent and Trademark Office*